(12) United States Patent
Mosko et al.

(10) Patent No.: US 7,781,375 B2
(45) Date of Patent: Aug. 24, 2010

(54) VOLUMIZING AGENTS

(75) Inventors: John T. Mosko, Perth Amboy, NJ (US); Richard C. Pluta, Towaco, NJ (US); David Michael Glenn, Shepherdstown, WV (US); Gary Puterka, Stillwater, OK (US)

(73) Assignee: Tessenderlo Kerley, Inc., Phoenix, AZ (US)

( * ) Notice: Subject to any disclaimer, the term of this patent is extended or adjusted under 35 U.S.C. 154(b) by 779 days.

(21) Appl. No.: 11/464,023

(22) Filed: Aug. 11, 2006

(65) Prior Publication Data

US 2007/0037712 A1 Feb. 15, 2007

Related U.S. Application Data

(63) Continuation-in-part of application No. 11/463,883, filed on Aug. 10, 2006.

(60) Provisional application No. 60/595,858, filed on Aug. 11, 2005.

(51) Int. Cl.
*A01N 59/06* (2006.01)
*A01N 25/00* (2006.01)
*A01N 25/24* (2006.01)

(52) U.S. Cl. .............. 504/187; 504/358; 504/360; 514/57; 514/781; 424/489

(58) Field of Classification Search ............ 504/367, 504/358, 360, 187; 514/57, 781; 501/144; 106/468, 486; 424/489
See application file for complete search history.

(56) References Cited

U.S. PATENT DOCUMENTS

| | | | | |
|---|---|---|---|---|
| 3,929,692 | A | * | 12/1975 | Offerman ............. 524/44 |
| 5,078,793 | A | * | 1/1992 | Caton ................ 106/417 |
| 5,720,967 | A | * | 2/1998 | Hall-Hibbitts et al. ...... 424/405 |
| 5,908,708 | A | | 6/1999 | Sekutowski |
| 6,027,740 | A | * | 2/2000 | Puterka et al. ......... 424/405 |
| 6,060,521 | A | | 5/2000 | Sekutowski |
| 6,069,112 | A | | 5/2000 | Glenn |
| 6,110,867 | A | | 8/2000 | Glenn et al. |
| 6,156,327 | A | | 12/2000 | Sekutowski |
| 6,235,683 | B1 | | 5/2001 | Glenn |
| 6,464,995 | B1 | | 10/2002 | Sekutowski |
| 6,514,512 | B1 | * | 2/2003 | Puterka et al. ......... 424/421 |

OTHER PUBLICATIONS

Cellosize Hydroxyethyl Cellulose (HEC) Product Sheet, Aug. 20, 2003; 13:29:35 CST [retrieved on Jul. 20, 2009]. Retrieved from the Internet: <URL:http://web.archive.org/web/20030820205049/http://www.dow.com/ucarlatex/prod/cello/>.*
Dhaliwal, Effect of Rainfall and Kaolinite Spray on the Corn Aphid, Rhopalosiphum Maidis (Fitch) Infesting Barley (Hordeum Vulgare Linn), Forage Res. 5, (1979), pp. 155-157.
Stanhill et al., "Effect of Increasing Foliage and Soil Reflectivity on the Yield and Water Use Efficiency of Grain Sorghum", Agronomy Journal, vol. 68, pp. 329-332, Mar.-Apr. 1976.
Moreshet et al. "Effect of Increasing Foliage Reflectance on Yield, Growth, and Physiological Behavior of a Dryland Cotton Crop", Crop Science, vol. 19, pp. 863-868, Nov.-Dec. 1979.
W. C. Bigelow, D. L. Pickett and W. A. Zisman, "Oleophobic Monolayers" J. Colloid Science, vol. 1, p. 513-537, (1946).
Sekutowski, D., "Fillers, Extenders, and Reinforcing Agents", Plastics Additives and Modifiers Handbook, Van Nostrand Reinhold, New York, 1992, pp. 493-500.

* cited by examiner

*Primary Examiner*—John Pak
*Assistant Examiner*—Andriae M Holt
(74) *Attorney, Agent, or Firm*—Hayden Stone PLLC; Christopher G. Hayden

(57) ABSTRACT

The present composition is capable of forming a particle film and comprises: (a) less than 99.65% by weight of at least one particle; (b) at least one volumizing agent selected from the group consisting of: (i) cellulose selected from the group consisting of ethyl hydroxy ethyl cellulose, hydroxy ethyl cellulose, hydroxy propyl cellulose, hydroxy ethyl methyl cellulose, hydroxy propyl methyl cellulose, methyl cellulose, ethyl cellulose, and ethyl methyl cellulose and present in an amount greater than 0.35% by weight; and (ii) non-cellulosic component or cellulose other than said cellulose (i) present in an amount of at least 0.05% by weight; and optionally (c) at least one spreader.

Figure 1:
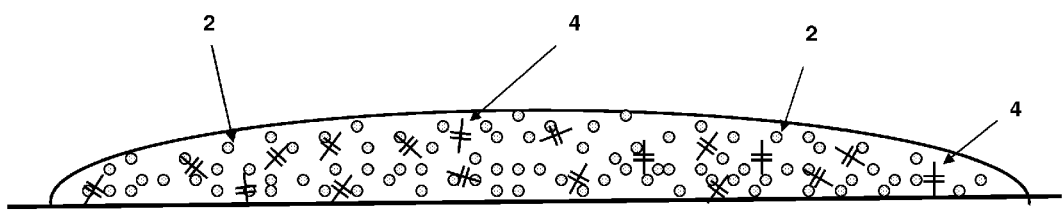

The composition may be used to form agricultural films.

15 Claims, 21 Drawing Sheets

VOLUMIZING AGENTS

This patent application claims priority to U.S. Provisional Patent Application Ser. No. 60/595,858 filed Aug. 11, 2005 and is a Continuation-in-Part of U.S. patent application Ser. No. 11/463,883 filed Aug. 10, 2006, incorporated herein by reference in their entireties.

BACKGROUND OF THE INVENTION

The importance of agriculture to the economy cannot be overstated. To foster strong agricultural production, a myriad of treatments for agricultural substrates exist. Such treatments are diverse and include pesticides, growth promoters, fertilizers, and the like. Increasing the effectiveness of these treatments is desirable as agricultural production is facilitated.

There are several factors commonly used to evaluate the effectiveness of topical agricultural or horticultural treatments.

One factor is the retention of the treatment on the plant surface for a time sufficient to achieve the desired result. In this connection, adequate retention times indicate that properties such as resistance to time, wind, water, mechanical or chemical action are possessed.

Another factor is proper coverage of the treatment to provide appropriate coverage over the plant surface. Proper coverage may involve modifying the surface tension of spray droplets, increasing surface wetting, and/or enhancing coverage.

Another factor is the nature of the deposition itself, which needs to be appropriate to maximize the effect of the application.

It is difficult to provide topical agricultural or horticultural treatments with desirable retention characteristics, desired deposition, and proper coverage. For example, often, improving retention characteristics results in reducing proper coverage, and vice versa. In another example, improving coverage can have undesirable deposition characteristics. A key strategy in applying to plants is the consideration of the hydrophobic to hydrophilic nature of plant surfaces. Also, substrate characteristics such as orientation, form, purity, texture, and rigidity are to be considered.

Agricultural treatment substrates are both hydrophobic and hydrophilic surfaces and these two groups are defined by the contact angle of a sessile droplet resting on the target surface. Target surfaces are considered hydrophilic when the contact angle of a water droplet is less than 90° and considered hydrophobic when the contact angle is greater than 90°.

The problems associated with the application of liquids to hydrophobic and hydrophilic surfaces are well known.

Applications of liquids to hydrophobic surfaces are problematic as these surfaces repel aqueous-based sprays. This is usually remedied by use of a surfactant. However, depositions with surfactants used by themselves can be too thin and can run off hydrophobic surfaces and, in addition, can be extremely thin and have extreme run off of co-targeted hydrophilic surfaces. Thus, in terms of hydrophilic surfaces, conventional agricultural surfactants (spreaders) used by themselves can overspread and cause extreme runoff resulting in poor coverage.

The application of liquids to hydrophilic surfaces poses fewer problems because these surfaces readily wet. The main problem encountered with applying liquids to hydrophilic surfaces is the phenomenon known as over-wetting that results in overspreading and can cause approximately two-thirds of the spray material to run off the surface and be wasted. Reducing spray volumes will generally reduce, but not eliminate, this problem.

These problems are also seen specifically in the delivery of agricultural particle films. There are two techniques currently used to improve delivery of particles to target surfaces. One is the retention of the treatment on the plant surface by the use of stickers. The second factor is the use of spreaders to improve coverage of the treatment. These arts can enhance spray retention on hydrophobic surfaces but overspreading and droplet retraction occurs which leads to the problem of thin, spotty deposits and/or non-uniform film formation. When spreaders are used in hydrophilic surfaces run off is a problem.

There is also a need for spreading and sticking agents that have relatively equal deposition properties on both hydrophobic and hydrophilic surfaces. This is particularly needed in plants that have both hydrophobic and hydrophilic surfaces such as tomatoes and grapes wherein generally the fruit is hydrophobic and the foliage is hydrophilic. In such a case, a given level of conventional spreaders may be ideal for the hydrophobic part of the plant, but may induce overspreading on the hydrophilic part of the plant.

SURROUND® WP crop protectant is labeled as 95% kaolin and 5% other ingredients. The specimen label discloses that initial application over waxy surfaces such as mango fruit may not spread and instructs the user to see Engelhard supplemental labeling for further information on use of spreaders. Commonly assigned U.S. Pat. No. 6,514,512 teaches that SURROUND® WP crop protectant is calcined kaolin with an organic spreader/sticker. However, in commercial usage and as seen in FIG. 9, SURROUND® WP crop protectant does not have film-forming spreading (defined below) on hydrophobic surfaces but adequate depositions do occur on hydrophilic surfaces.

Particle films are used for sunburn and heat stress reduction and rely on the light properties passing through the particle film, in particular the controlled blockage of visible, UV, and IR light, to gain beneficial effects. Improved particle film treatments with improved controlled blockage of light and film-forming spreading (defined below) for both hydrophilic and hydrophobic agricultural substrates are therefore desired.

SUMMARY OF THE INVENTION

The following is a summary of the invention in order to provide a basic understanding of some aspects of the invention. This summary is not intended to identify key/critical elements of the invention or to delineate the scope of the invention. Its sole purpose is to present some concepts of the invention in a simplified form as a prelude to the more detailed description that is presented later.

The present composition is capable of forming a particle film and comprises: (a) less than 99.65% by weight of at least one particle; (b) at least one volumizing agent selected from the group consisting of: (i) cellulose selected from the group consisting of ethyl hydroxy ethyl cellulose, hydroxy ethyl cellulose, hydroxy propyl cellulose, hydroxy ethyl methyl cellulose, hydroxy propyl methyl cellulose, methyl cellulose, ethyl cellulose, and ethyl methyl cellulose and present in an amount greater than 0.35% by weight; and (ii) non-cellulosic component or cellulose other than said cellulose (i) present in an amount of at least 0.05% by weight; and optionally (c) at least one spreader.

The present invention provides a composition that is capable of forming a particle film comprising: (a) less than 99.5% by weight of at least one particle; (b) at least 0.5% by weight of a volumizing agent (defined below); and optionally (c) at least one spreader.

In one example, the present composition comprises: (a) particles, and (b) gelatin. The volumizing agents of (b) do not, per se, have the ability to spread on hydrophobic surfaces. The present composition forms volumized films when wet or dry. At least one of the following may also be present: a conventional agricultural spreader, polymeric film-forming agent, agricultural sticker, functional additive, or facilitator.

The volumized nature of the particle film composition contributes to the ability of the film to provide numerous agricultural benefits.

A main benefit of volumization is the increase in opacity known to occur via the phenomena of scattering of light due to flocking or flocculation of the particles. It is known that if air interfaces are created between particles much like a house of cards, light scattering, and therefore opacity, is increased, This phenomena is seen in such substances as snow (versus ice) and crushed glass (versus uncrushed glass). Products for paper coatings, for example, have utilized this phenomenon to increase opacity in paper. Via achievement of volumization as taught herein, a marked increase in opacity is seen. Using volumization agents, hydrous kaolin particle film compositions can be prepared that perform like, or better than, particle film compositions using the more expensive calcined kaolins.

Certain volumization agents achieve high opacity particle film compositions on hydrophilic surfaces with film-forming spreading (defined below).

Certain volumization agents act as an effective spreading inhibitor. The phrase "spreading inhibitor" as used herein means a substance that has both low spreading on hydrophobic surfaces and may prevent other known spreaders from spreading. Examples of spreading inhibitors include low molecular weight hydroxylethyl cellulose (HEC) and carboxymethyl cellulose (CMC). In this way, novel depositions, for example, can be attained with compositions that do not spread on hydrophobic surfaces thus forming purposely discontinuous or spotty coverage that can be advantageous for enhanced insect repellency.

Compositions can thus be made which selectively deposit on the part of the plant where the deposition is desired but resist depositing on the part of the plant where deposition is not desired. An example is grapes, where it may be desirable to treat the (hydrophilic) leaves for protection against insects but it is preferred to reduce the amount deposited on the (hydrophobic) grape berries.

Further novel compositions can be made with volumizing agents and spreading agents to achieve film-forming spreading on hydrophobic surfaces that is similar to the film-forming spreading achieved on hydrophilic surfaces (including a co-sprayed hydrophilic surface).

Volumized compositions maximize the height of the deposition and increase friability of the particle film.

BRIEF DESCRIPTION OF THE DRAWINGS

FIGS. 1 through 8 represent idealized operation of known compositions and the present compositions.

FIGS. 9 through 25 are photographs of various surfaces having either known compositions or the present compositions applied thereon.

DETAILED DESCRIPTION OF THE INVENTION

The term "flock" or "flocking" as used herein means using physical or chemical means to achieve an association of two or more individual particles in the wet or dry state. This effect is known as flocculation.

The term "flocked" as used herein means an association of individual particles in the wet or dry state.

The term "structure" or "structuring" as used herein means having the ability to cause individual particles to form flocks, agglomerates, aggregates, and/or associations that can cause a system to be volumized upon drying and thereby constructs a functional deposition.

The term "structured" as used herein means two or more individual particles that have formed flocks, agglomerates, aggregates, and/or otherwise associated that cause a system to be volumized.

The term "volumized" as used herein means the increased separation of a given mass of particles. Volumized usually results from structuring as defined above or may also result from increasing viscosity and/or surface tension. In most cases, this means that the resultant dried deposition, wet deposition or wet sediment has a greater volume than the same deposition that is not volumized. Volumized also means that depositions are higher and thicker in the liquid state (before drying).

The phrase "volumizing agent" as used herein means any agent capable of constructing a volumized system that does not spread, per se, on hydrophobic surfaces, but spreads readily on hydrophilic surfaces.

The term "sticker" as used herein means a material that increases the adhesion of sprays on plants by resisting various environmental factors. Sticker may also increase the firmness of attachment of spray emulsions, active ingredients, water soluble materials, liquid chemicals, finely-divided solids or other water-soluble or water-insoluble materials to a solid surface, and which may be measured in terms of resistance to time, wind, water, mechanical or chemical action.

A sticker may be further defined as a material which increases spray droplet retention to a substrate by facilitating droplet capture and thereby preventing the material from rolling off, blowing off, deflecting, shattering, or otherwise reducing the amount of spray material which remains in contact on the substrate during moment of deposition until the time which the spray droplet has chance to dry.

The word "film" as used herein means a wet or dry coating that is either continuous or discontinuous on a substrate.

The phrase "particle film" as used herein means a film composed substantially of particles.

The term "spreading" as used herein means a method to increase the area that a given volume of liquid covers a substrate.

The term "spreading agent" as used herein means an agent that achieves spreading as defined herein.

The term "film forming spreading" as used herein means a type of spreading that also builds films having increased fluid volume retention and thus increased solids deposition on similarly both hydrophilic and hydrophobic surfaces.

Volumizing Agent

A volumized particle film results in a higher level of efficiency per number of particles per a given mass of film. Due to the volumized and/or flocked or otherwise associated structure, several advantages are obtainable. The volumized particle film has highly separated particles. The volumized film exhibits improved elastic properties, flexural properties and energy buffering properties making it less vulnerable to cracking, chipping, an/or flaking, thereby improving weatherability by reducing wash-off and wind attrition while improving adhesion. The volumized particle film is less likely than a conventional spread film to have its particles deeply embedded in the waxy cuticle of fruit. When employing particles on plants, the volumized particle film improves scattering of undesirable or excessive infrared, visible, and ultraviolet light. Also, because more uniform depositions are produced, more uniform light is transmitted to the substrate resulting in more uniform color and less mottling. The volumized particle film has improved insect control compared to a conventional spread film due to its increased friability, greater surface area and greater number and mass of particles available to contact the pest.

The volumized particle film slurry has a contact angle that is able to form a volumized structure. Contact angles may be determined according to any suitable known method, including the Sessile Drop Method first developed by Zisman, W. A., et al., J. Colloid Sci., Vol. 1, p. 513 (1946). For example, a substrate can be placed on a flat plate in a Rane Hart goniometer and a volumized film of interest is formed on the substrate. The angle is read from the viewer, after adjusting the baseline. Other contact angle measuring instruments are made by ATI Cahn Instruments, Inc. and Elma Kogaku Co., Ltd., both of which incorporate different methods of analysis.

This invention concerns volumizing agents that do not have the ability per se to spread on hydrophobic surfaces. These volumizing agents may be of relatively low to moderate molecular weight compared to others in their class and lack sufficient lipophilicity to induce spreading.

Examples of such volumizing agents include glues, gelatins, collagens, hydrolyzed collagens, magnesium aluminum silicates, colloidal clays, cellulose polymers, polyacrylates, polyacrylamide (PAM), polyamines (epichlorohydrin-dimethylamine); polydiallyldimethylammonium chloride (poly-DADMAC), epichlorohydrin-dimethylamine (Epi-DMA), and gums such as locust bean gum, xanthan gum, guar gum, carrageenan, Psyllium.

Glues are generally considered to be adhesives consisting of organic colloids of a complex protein structure obtained from animal materials such as bones and hides in meat packing and tanning industries. Glues generally contain two groups of proteins: namely, chondrin and glutin. Animal glue is a protein derived from the hydrolysis of collagen, which is the principal protein constituent of animal hide, connective tissue, and bones. Gelatin is one of the main constituents of animal glue, which is derived from the waste skins and cuttings from tan yards together with bones, skins, tendons, horn piths, etc. from slaughterhouses. The preceding mixture is washed with water and then treated for up to 30 days by soaking in limewater to remove hair and flesh. The resulting product is rinsed with several washes of water and sometimes also with very dilute acid to prevent bacterial decomposition. Hide glue and bone glue make up the two major types of animal glue. Bone glue is made from bone meal that had been washed with benzene of carbon tetrachloride to remove grease. Bone glue is processed from the collagen content of bones, mainly from bones of bovine animals. Bone glue prepared from solvent-extracted, degreased bones is extracted bone glue.

Gelatin materials include gelatin, collagen, and glue and are commercially available from a number of sources including Milligan and Higgins, Extraco, U.S. Adhesives, National Starch & Chemical, and J. Hewit & Sons Ltd. Gelatin materials are typically in powder, sphere, or granular form. While not wishing to be bound by any theory, it is believed that the gelatin materials facilitate the formation of particulate material agglomerates as well as facilitate binding between particulate material agglomerates and substrates.

Examples of magnesium aluminum silicates and colloidal clays include attapulgites and bentonites. Attapulgites and bentonites may be beneficiated or otherwise processed. Useful attapulgite is commercially available from Engelhard Corporation.

Cellulose polymers are complex carbohydrates (polysaccharides) of thousands of glucose units in a generally linear chain structure. Celluloses are generally water-soluble polymers. Celluloses include one or more of non-hydrolyzed, partially hydrolyzed, substantially hydrolyzed, and fully hydrolyzed celluloses.

Examples of celluloses specifically include ethyl hydroxy ethyl cellulose, hydroxy ethyl cellulose, hydroxy propyl cellulose, hydroxy ethyl methyl cellulose, hydroxy propyl methyl cellulose, methyl cellulose, carboxy methyl cellulose, sodium carboxy methyl cellulose, ethyl cellulose, ethyl methyl cellulose, cross-linked sodium carboxymethyl cellulose, enzymically hydrolyzed carboxymethylcellulose, and the like. Celluloses are commercially available from numerous sources including Dow (under the product designation Methocel®, for example) and Hercules (Aqualon Division).

Cellulose volumizing agents have the ability to create a purposely discontinuous or spotted film on surfaces. This trait is useful in creating spotted particle films deposition patterns that can disguise fruit or crops from insects such as fruit flies, thus lowering insect damage. Examples of cellulose types that form spots on hydrophobic surfaces are hydroxylethyl cellulose, carboxy methyl cellulose, sodium carboxy methyl cellulose, cross-linked sodium carboxymethyl cellulose, enzymically hydrolyzed carboxymethylcellulose, and the like.

Polyacrylates have the repeating unit $—[CH_2—CR(CO_2R)]_n—$ wherein each R is independently a hydrogen, or alkoxy or alkyl group containing 1 to about 4 carbon atoms, and n is from about 250 to about 10,000. In another embodiment, each R is independently a hydrogen or methyl group and n is from about 500 to about 5,000 Daltons. Examples include polymethylacrylate, polyethylacrylate, polyacrylic acid, polymethylmethacrylate, polyethylmethacrylate, poly (2-hydroxyethyl methacrylate), and the like. High molecular weight polyacrylamides are commercially available from a number of sources including SNF Floerger of France and Jinke Chem of China.

Some volumizing agents have the ability to form tall depositions by virtue of limiting the surface coverage of the incompatible substrate. These tall depositions can have a haystack-shaped structure that results in high friability or looseness of the particles. This trait can be advantageous for example in insect control.

In addition, finely divided, low density (<1.0 g/m) insoluble materials, materials minimally or partially soluble, or materials from the above group which are minimally soluble may function as volumizing agents via buoyancy and density differences. Examples include cross-linked polyvinyl alcohols, fully hydrolyzed polyvinyl alcohols, micronized thermoplastics, and powdered waxes.

Foaming agents may be used as volumizing agents as the gas entrained in the application has the capability to create extremely volumized and friable systems. Some examples of foaming agents are detergents, proteinaceous substances, and water-soluble polymers (higher molecular weights preferred).

By nature the soluble volumizing agents disclosed above are effective foaming agents.

Spreader:

The present composition may additionally comprise a conventional agricultural spreader that causes the volumized composition to attain film-forming spreading similarly effectively on both hydrophobic and hydrophilic surfaces. Such products can increase spreading and thus coverage area of volumized compositions that normally resist spreading on incompatible surfaces (usually hydrophobic). These spreaders are composed of a surfactant or surfactants and other ingredients that improve film-formation.

Conventional spreaders are nonionic, anionic, cationic, or amphoteric. Examples include modified phthalic glycerol alkyd resins such as Rohm & Haas' Latron B-1956, plant oils such as cotton seed oil or cocodithalymide such as Sea-wet from Salsbury Lab, polymeric terpenes such as Pinene II from Drexel Chem., and ethoxylated tall oil fatty acids such as Toximul 859 and Ninex MT-600 from Stepan.

Other useful spreaders include nonionics such as alkyl polyglucosides and octylphenol ethyoxylates, and anionics such as dioctyl sulfosuccinates, phosphate esters, sulfates, or sulfonates such as Dow's Triton™ products. Other useful spreaders include nonionics such as branched secondary alcohol ethoxylates, ethylene oxide/propylene oxide copolymers, nonylphenol ethoxylates, and secondary alcohol ethoxylates such as Dow's Tergitol™ products. Other useful spreaders include organosilicones such as Silwet and phenoxyethanol such as Igepal.

Particles:

The base particles used in the dry mixture and the slurries can be hydrophobic or hydrophilic. The particles can be hydrophobic in and of themselves, (for example, mineral talc). Alternatively, the particles can be hydrophilic materials that are rendered hydrophobic by application of a surface treatment such as a hydrophobic wetting or coupling agent; for example, the particle has a hydrophilic core and a hydrophobic outer surface. In another alternative embodiment, the particles are hydrophilic in and of themselves, for example calcined kaolins. In yet another embodiment, the particles are hydrophobic in and of themselves and made hydrophilic by the addition of wetting agents such as surfactants or emulsifiers.

Examples of base particles suitable for use in the present invention includes processed minerals, such as water processed kaolin; air processed kaolin; hydrous kaolin; calcined kaolin; anhydrite; sillimanite group minerals such as andalusites, kyanites, sillimanites; staurolite, tripoli; tremolite; gypsum (natural and synthetic); anhydrite; asbestos materials; adobe materials; barites; bauxite or synthetic aluminum trihydrate; fine aggregated material less than 50 u median PSD, both lightweight and dense such as crushed or milled stones, gravels, silicas, silica flours, pumices, volcanic cinders, slags, scorias, expanded shales, volcanic cinders, limestones such as calcites and dolomites; diamond dusts both synthetic and natural; emerys; biotites; garnets; gilsonites; glauconites; vermiculites, fly ashes, grogs (broken or crushed brick), shells (oyster, coquina, etc.); wash plant or mill tailings, phosphate rocks; potash; nepheline syenites, beryllium materials such as beryls; borons and borates, calcium carbonates both ground and precipitated, talcs, clay minerals such as fullers earths, ball clays, halloysites, refractory clays, flint clays, shales, fire clays, ceramic clays, coal containing kaolins, bentonites, smectites (montmorillonite, saponites, hectorites, etc); hormites (attapulgites, pyrophyllites, sepeolites, etc.); olivines; feldspars; sands; quartz; chalks; diatomaceous earths; insulation materials such as calcium silicates, glass fibers, mineral wools or rock wools; wollastonites; graphites; muscovites; micas; refractory materials; vermiculites; perlites; glass fibers; rare earth minerals; elemental sulfurs and other sulfur minerals; other insoluble elemental and salt compounds; other miscellaneous insoluble particles; other functional fillers such as, pyrogenic silicas, titanium minerals such as titanium dioxides, magnesium oxides, magnesite.

Examples of non-mineral base hydrophilic particles include carbon soot, coal dust, ash waste and other colored organic materials. Organic materials such as cellulose fibers; wood fiber; vegetable fibers such as bamboo, hemp, jute, sisal and the like; synthetic fibers such as nylon, aramid, polyethylene, polytetrafluroethylene; animal fibers such as wool, etc.

All materials may be considered useful to this invention whether incorporated in their natural/crude/hydrous form, in processed forms including water washing, air floated, beneficiated, and synthetically produced. Further processing can include heat treatment above 400 degrees Fahrenheit, more commonly referred to as calcination.

Heat treatment in accordance with the invention commonly involves heating a particle at a temperature from about 100° C. to about 1,200° C. for about 10 seconds to about 24 hours. In another embodiment, heat treatment involves heating a particle at a temperature from about 400° C. to about 1,100° C. for about 1 minute to about 15 hours. In yet another embodiment, heat treatment involves heating a particle at a temperature from about 500° C. to about 1,000° C. for about 10 minutes to about 10 hours. The heat treatment may be carried out in air, in an inert atmosphere or under a vacuum.

Examples of heat-treated base particles are particles that have been heated to an elevated temperature and include baked particles, calcined particles, and fired particles. Heat-treated particles are generally hydrophilic. Specific examples include metakaolin, calcined calcium carbonate, calcined talc, calcined kaolin, baked kaolin, fired kaolin, hydrophobic treated heat treated kaolin, calcined bentonites, calcined attapulgite, calcined clays, calcined pyrophyllite, calcined silica, calcined feldspar, calcined sand, calcined quartz, calcined chalk, calcined limestone, calcined precipitated calcium carbonate, baked calcium carbonate, calcined diatomaceous earth, calcined barytes, calcined aluminum trihydrate, calcined pyrogenic silica, and calcined titanium dioxide.

In these embodiments, the particles contain at least about 10% by weight, and particularly 25% to about 100% by weight of heat-treated particles. In another embodiment, the particles contain at least 40% by weight, and particularly about 40% to about 99% by weight heat-treated particles.

The surfaces of the particulate hydrophilic materials can be made hydrophobic by coating the particle with at least one hydrophobic agent. Industrial mineral applications, especially in organic systems such as plastic composites, films, organic coatings or rubbers, utilize hydrophobic surface treatments to render a mineral surface hydrophobic; see, for example, Jesse Edenbaum, Plastics Additives and Modifiers Handbook, Van Nostrand Reinhold, New York, 1992, pages 497-500 which is incorporated herein by reference for teachings of such hydrophobic surface treatment materials and their application.

These surface treatment materials include coupling agents such as fatty acids and silanes are commonly used to surface treat solid particles to render them hydrophobic. Examples of hydrophilic materials that are made hydrophobic include organic titanates such as Tilcom® from Tioxide Chemicals; organic zirconate or aluminate coupling agents from Kenrich Petrochemical, Inc.; organofunctional silanes such as vinyl-triethoxysilane; vinyl tris-(2-methoxyethoxy)silane; γ-methacryloxypropyltrimethoxysilane; β-(3,4-epoxycyclohexyl) ethyltrimethoxysilane; γ-glycidoxypropyltrimethoxysilane; γ-mercaptopropyltrimethoxysilane; γ-aminopropyltriethoxysilane; N-β-(aminoethyl)-γ-aminopropyltrimethoxysilane; and β-mercaptoethyltriethoxysilane, and others under the trade designation Silquest® from Witco or those under the trade designation Prosil® from PCR; modified silicone fluids such as the DM-Fluids obtained from Shin Etsu; and fatty acids such as double pressed stearic acid and triple pressed stearic acid and others under the trade designation Hystrene® or Industrene® from Witco Corporation or those under the trade designation Emersol® from Henkel Corporation. In a specific embodiment, stearic acid and stearate salts are particularly effective for rendering a particle surface hydrophobic.

In these embodiments, the particles contain at least about 10% by weight, and particularly 25% to about 100% by weight of heat-treated particles. In another embodiment, the particles contain at least 40% by weight, and particularly about 40% to about 99% by weight heat-treated particles.

The particles suitable for use in the present invention are finely divided. The term finely divided when utilized herein means that the particles have a median individual particle size (average diameter) below about 100 μm. In one embodiment, the particles have a median individual particle size of about 10 μm or less. In another embodiment, the particles have a median individual particle size of about 3 μm or less. In yet another embodiment, the particles have a median individual particle size of about 1 μm or less.

Particle size and particle size distribution as used herein are measured with a Micromeritics Sedigraph 5100 Particle Size Analyzer. Measurements are recorded in deionized water for hydrophilic particles. Dispersions are prepared by weighing 4 grams of dry sample into a plastic beaker, adding dispersant and diluting to the 80 ml mark with deionized water. The slurries are then stirred and set in an ultrasonic bath for 290 seconds. Typically, for kaolin 0.5% tetrasodium pyrophosphate is used as a dispersant; with calcium carbonate 1.0% Calgon T is used. Typical densities for the various powders are programmed into the sedigraph, for example, 2.58 g/ml for kaolin. The sample cells are filled with the sample slurries and the X-rays are recorded and converted to particle size distribution curves by the Stokes equation. The median particle size is determined at the 50% level.

The particles suitable for use in the present invention may have any shape including plate-like, spherical, cylindrical, oval, cubic, amorphous, toothpick like, popcorn like, and the like.

Functional Additives:

The present invention may also include other functional additives.

One example of a functional additive is cross-linking agents. Cross-linking agents, when combined with cross-linkable polymers, facilitates the formation of a volumized system. The cross-linking agent reacts with the cross-linkable polymers to increase the molecular weight. Examples of cross-linking agents include borax, glyoxal, alkylene glycol methacrylates, ureaformaldehyde, and the like. As an example of a cross-linked polymer, a high molecular weight polyvinyl alcohol may be cross-linked with borax or polyacrylamide may be cross-linked with ethylene glycol dimethacrylate.

Another example of a functional additive is dark pigments. Useful dark pigments include yellow iron oxides such as goethite (synthetic and natural), lepidocrocite (synthetic and natural), ochres, siennas, limonite, akagenite; Red iron oxide pigments such as hematite (synthetic and natural), siderite (natural and calcined), pyrites (natural and calcined); Brown iron oxide pigments such as umbers, limonite (natural and calcined), siderite (natural and calcined), goethite (bog ore or sulfur mud), synthetic pigments such as blends of hematite, goethite and magnetite, co-precipitated hematite-magnetite, maghemite; Black iron oxide pigments such as magnetite (natural and synthetic), slate (mixed minerals), gilsonites, glauconites, coal kaolins, and the like.

In another embodiment where the slurry contains water, the particle mixture, and optionally further additives, the further additives include low boiling organic liquids, high boiling organic liquids, pest control agents such as pesticides, fungicides, insecticides, etc., an emulsifying agent, a suspending agent, a penetrating agent, a wetting agent, a thickening agent, a stabilizer, nutrients, microbial agents, fertilizers, herbicides, etc. The slurry may be formed by combining the components in any order, followed by mixing.

The low boiling organic liquids include water-miscible and organic solvents. In one embodiment, the low boiling organic liquids contain from 1 to about 6 carbon atoms. The term low boiling as used herein means organic liquids that have a boiling point generally no higher than about 100° C. These liquids promote the ability of the particle mixture to remain in a finely divided state without significant agglomeration. Examples of low boiling organic liquids include alcohols such as methanol, ethanol, propanol, i-propanol, butanol, i-butanol, and the like, glycols (polyols), ketones such as acetone, methyl ethyl ketone and the like, and cyclic ethers such as ethylene oxide, propylene oxide and tetrahydrofuran. Combinations of the above-mentioned low boiling organic liquids, with or without water, can also be employed.

Low boiling organic liquids may be employed to facilitate applying the particle mixture by spraying to target surfaces. Typically, the low boiling organic liquids are used in an amount sufficient to facilitate the formation a dispersion of the particle mixture. In one embodiment, the amount of low boiling organic liquid is up to about 30% (volume percent) of the dispersion. In another embodiment, the amount of low boiling organic liquid is from about 1% to about 20% (volume percent) of the dispersion. In yet another embodiment, the amount of low boiling organic liquid is from about 2% to about 10% (volume percent) of the dispersion. The particle mixture is preferably added to a low boiling organic liquid to form a slurry and then this slurry is diluted with water to form an aqueous dispersion.

High boiling organic liquids including oils and fatty acids may be employed in applying the particle to substrates. The term high boiling as used herein means organic liquids that have a boiling point generally higher than about 100° C. Typically, the high boiling organic liquids and/or oils are used in an amount sufficient to facilitate the formation of a dispersion of the particle mixture. In one embodiment, the amount of high boiling organic liquid is up to about 30% (volume percent) of the dispersion. In another embodiment, the amount of high boiling organic liquid is from about 1% to about 20% (volume percent) of the dispersion. In yet another embodiment, the amount of high boiling organic liquid is from about 2% to about 10% (volume percent) of the dispersion. The particle is added to a high boiling organic liquid and/or oil to form a slurry, or the particle mixture is added to a high boiling organic liquid and/or oil with water to form an emulsion-slurry.

Examples of high boiling organic liquids include vegetable, industrial, marine, and paraffin oils including cottonseed oil, palm oil, peanut oil, corn oil, soya oil, castor oil, linseed oil, rapeseed oil, tung oil, oiticia oil, fish oil, sperm oil, Menhaden oil, and the like. Further examples of high boiling organic liquids include fatty acids such as saturated and unsaturated fatty acids including C6 to C32 carboxylic acids. Specific examples include caproic acid, caprylic acid, pelargonic acid, capric acid, lauric acid, myristic acid, pentadecyclic acid, palmitic acid, margigaric acid, strearic acid, lauroleic acid, myristoleic acid, palmitoleic acid, oleic acid, linoleic acid, linolenic acid, and the like. Commercially available oils include Orchex® products from Exxon, Volck oils from Chevron, Pennzspray® products from Pennzoil-Quaker State, and Sunspray® products from Sunoco.

Utility:

The volumized particle film may be used for pest/insect control, disease control, pesticide delivery systems, solar protection/reducing sunburn, ground-applied light reflectants, heat stress reduction, preventing damage from freezing temperatures, weed control, reducing physiological disorders such as watercore, corking and bitterpit, increasing the resistance to freeze dehydration, and the like.

In one embodiment, the volumized particle film slurry has a contact angle from about 45° to about 135° relative to the substrate. In another embodiment, the volumized particle film slurry has a contact angle from about 50° to about 130° relative to the substrate. In yet another embodiment, the volumized particle film slurry has a contact angle from about 60° to about 120° relative to the substrate. The current invention allows for the improved delivery of a desired contact angle that may be approximately 90 degrees to a wide variety of target substrates and is generally less dependent on the contact angle of said target substrate.

The volumized particle film having a volumized structure and/or a flocked or otherwise associated structure maximizes separation between particles that are contained therein. In this context, the volumized particle film may possess a relatively low solids content compared to a typical spread film. In some instances, the volumized particle film has a "house of cards" type structure for the particles contained therein.

Advantages over the current art of agricultural particle films include lower use rates, increased solar protection at an equal rate, and the improvement of the performance of normally inferior performing particles.

The present invention facilitates the application of a water-based, topical coating to produce a substantially uniform film over a variety of hydrophilic and hydrophobic target substrates that can be wet or dry, or result in a dry film upon drying.

The surfaces to which the present invention is applied may be porous and nonporous, homogeneous and heterogeneous, solid, liquid or gaseous, hydrophobic and hydrophilic surfaces that are smooth or rough, and can be purified, oxidized, contaminated or otherwise modified. Examples of surfaces include but are not limited to any natural surface including plant and animal surfaces, or surfaces of man-made structures, or other natural and man-made surfaces. Plant surfaces include those found on crops, household and ornamental plants, greenhouses, forests with types of surfaces that include leaves, stems, roots, trunks, or fruits, and include soil or other growth mediums, and the like. Examples of animal surfaces include those found on man, birds, arthropods, molluscs, cattle, sheep, horses, chickens, dogs, cats, fish and the like with types of surfaces that include skin, hair, fur, feathers, cuticles, wounds, and the like. Examples of man-made structures include, but is not limited to, those found on walls, floors, shelves, ceilings, stairs and the like in buildings, barns, pens, cages, animal bedding, greenhouses, electrical boxes and the like. Examples of man-made surfaces include metal, alloys, paper, ceramics, glass, concrete, plastic, polystyrene, asphalt, lumber, and the like. Examples of natural surfaces include hides, soil, stone, sand, crude oils, tars, water, ice, wood, lumber, and the like. All of such surfaces shall be collectively referred to as target surfaces. The substrates on which the volumized film may be formed can include horticultural crops such as actively growing agricultural crops, fruiting agricultural crops, actively growing ornamental crops, fruiting ornamental crops and the products thereof, and surfaces pests infest such as man-made structures, soil, and stored grains/fruits/nuts/seeds, as well as the surfaces of pests. Specific examples include fruits, vegetables, trees, flowers, grasses, and landscape plants and ornamental plants. Specific examples of plants include apple trees, pear trees, peach trees, plum trees, lemon trees, grapefruit trees, avocado trees, orange trees, apricot trees, walnut trees, raspberry plants, strawberry plants, blueberry plants, blackberry plants, boysenberry plants, corn, beans including soybeans, squash, tobacco, roses, violets, tulips, tomato plants, grape vines, pepper plants, wheat, barley, oats, rye, triticale, and hops. Man-made structures include buildings, storage containers, dwellings made of various materials such as plastics, wood, stone, cement, and metal. All of such substrates shall be collectively referred to as agricultural substrates. Pests include bacteria, fungus, worms including nematodes, insects, arachnids such as spiders and mites, snails, slugs, other molluscs, birds, rodents, deer, rabbit, and undesirable vegetation (weeds).

The slurry is applied to the target surfaces by spraying, or other suitable means. The particle treatment may be applied as one or more layers. The amount of material applied varies depending upon a number of factors, such as the identity of the substrate, the purpose of the application, and the identity of the particle, etc. In any given instance, the amount of material applied can be determined by one of ordinary skill in the art. The amount may be sufficient to form a continuous film or intermittent film over all or a portion of the substrate to which the particle treatment is applied. One or more layers of this dust, slurry, cream or foam may be dusted, sprinkled, sprayed, foamed, brushed on or otherwise applied to the surface. The resultant particle film residue, whether formed by a dry or slurry application, may result in coatings that are hydrophilic or hydrophobic.

The volumized particles can be applied in the form of colloidal particles, dispersions, spray dried beads, powders, agglomerates, microspheres, blends and the like.

The particle treatment may form a continuous layer. By continuous, it is meant that, where applied, the film, a wet or a resultant dry film, is continuous (or substantially, or semi-continuous). For example, in an embodiment where the upper third of a fruit is covered with particle mixture in accordance with the present invention, the film covering the upper third of the fruit is continuous or substantially continuous while the bottom two-thirds of the fruit is not covered with the particle mixture or forms a spotted or discontinuous film/deposition.

Typically, the thickness of the particle film applied using slurry ranges from about 1 μm to about 5,000 μm. In another embodiment, the thickness of the particle film ranges from about 3 μm to about 3,000 μm. In yet another embodiment, the thickness of the particle film ranges from about 5 μm to about 750 μm.

The present agricultural compositions may be used to enhance photosynthesis as disclosed in U.S. Pat. No. 6,110, 867, incorporated in its entirety herein by reference. Photosynthesis is the process by which photosynthetic plants utilize solar energy to build carbohydrates and other organic molecules from carbon dioxide and water. The conversion of carbon dioxide to such organic molecules is generally referred to as carbon fixation or photosynthesis and, in most plants, occurs by the reductive pentose phosphate cycle, generally referred to as the C-3 cycle. The study of the path of carbon in photosynthesis four decades ago (A. A. Benson (1951), "Identification of Ribulose in $^{14}CO_2$ Photosynthesis Products" *J. Am. Chem. Soc.* 73:2971; J. R. Quayle et al. (1954), "Enzymatic Carboxylation of Ribulose Diphosphate" *J. Am. Chem. Soc.* 76:3610) revealed the nature of the carbon dioxide fixation process in plants. Enhanced or improved photosynthesis is evidenced by increased carbon dioxide uptake or assimilation. Enhanced photosynthesis has many benefits including increased yields/productivity, e.g., increased fruit size or production (usually measured in weight/acre), improved color, increased soluble solids, e.g. sugar, acidity, etc., reduced plant temperature, increased storage life, increased turgor.

The present agricultural composition may be applied from about 25 up to about 5,000 micrograms of particle per $cm^2$ of surface for particles having specific density of around 2-3 $g/cm^3$, more typically from about 100 up to about 3,000, and preferably from about 100 up to about 500. In addition, environmental conditions such as wind and rain may reduce coverage of the particle and therefore, multiple applications may be desirable.

In one embodiment, the volumized films made in accordance with the present invention do not materially affect the exchange of gases on the target surface. The gases that pass through the particle treatment (or residue from the inventive treatment) are those that are typically exchanged through the target surface and the environment (for example: plant, soil or plant-producing surfaces, mammalian skin, fur or other surfaces). Such gases, vapors or scents include water vapor, carbon dioxide, oxygen, nitrogen, volatile organics, fumigants, pheromones and the like.

Trees such as apple trees have stomates with apertures averaging about 14 microns. Plants such as cotton plants have stomates with apertures averaging about 19 microns. Since gases such as carbon dioxide enter plants through their stomates, one skilled in the art would select a plant and then a composition particle size and amount appropriate for that plant to achieve the desired result.

In another embodiment, the particles may be used to form a gas impermeable film that restricts the exchange of gases on the surface of the substrate. The gases, which do not pass through the particle treatment of this embodiment, are those that are typically exchanged through the substrates and the environment (for example: plant, soil or plant-producing surfaces, mammalian skin, fur or other surfaces). Such gases, vapors or scents include water vapor, carbon dioxide, oxygen, nitrogen, volatile organics, pheromones, fumigants and the like.

The present agricultural composition may be used in the particle film applications disclosed in U.S. Pat. Nos. 5,908,708; 6,027,740; 6,060,521; 6,069,112; 6,156,327; 6,235,683; 6,464,995; and 6,514,512, all incorporated in their entirety herein by reference.

The particles can be incorporated into dry mixtures such as wettable powders or wet mixtures such as liquids, emulsions, slurries, creams, foams or pastes. The mixtures can be applied as sprays, dips, brushed, rubbed or otherwise topically applied to a target surface. The particles used can be either hydrophobic or hydrophilic. In one embodiment, the particles are hydrophobic in and of themselves, (for example, mineral talc). In another embodiment, the particles are hydrophilic materials that are rendered hydrophobic by application of an outer coating of a suitable hydrophobic wetting agent or coupling agent (for example, in an embodiment where a particle has a hydrophilic core and a hydrophobic outer surface). In yet another embodiment, the particles are hydrophilic in and of themselves (calcined kaolins).

When high molecular weight polymeric film forming material, water-insoluble cross-linkable polymeric film forming material, structuring agent, and/or cross-linking agents in the powder form are used, the powder has a median individual particle size (average diameter) below about 500 µm. In another embodiment, the powder has a median individual particle size below about 350 µm. In yet another embodiment, the powder has a median individual particle size below about 200 µm.

When high molecular weight polymeric film forming material, water-insoluble cross-linkable polymeric film forming material, structural agent, and/or cross-linking agent in the powder form are used, a premix containing the particles and one or more of the high molecular weight polymeric film forming material, water-insoluble cross-linkable polymeric film forming material, structural agent, and/or cross-linking agent may be provided. In one embodiment, the premix contains about 1% by weight or more and about 40% by weight or less of one or more of high molecular weight polymeric film forming material, water-insoluble cross-linkable polymeric film forming material, structural agent, and/or cross-linking agent and about 60% by weight or more and about 99% by weight or less of the particles (all %'s dry weight). In another embodiment, the premix contains about 2% by weight or more and about 30% by weight or less of one or more of high molecular weight polymeric film forming material, water-insoluble cross-linkable polymeric film forming material, structural agent, and/or cross-linking agent and about 70% by weight or more and about 98% by weight or less of the particles.

In one embodiment, the application of the particulate mixture can be applied to the target surface as a slurry of particles in a volatile liquid such as water, a low boiling organic solvent or low boiling organic solvent/water mixtures. In yet another embodiment, the particulate mixture can be applied to the target surface as a paste, cream or foam based on low or high organic solvent/water mixtures. One or more layers of this dust, slurry, cream or foam can be dusted, sprinkled, sprayed, foamed, brushed on or otherwise applied to the target surface. The resultant residue, whether formed by a dust or slurry application, may be hydrophilic or hydrophobic.

In another embodiment where the slurry contains water, the particle mixture, and optionally further additives, the further additives include low boiling organic liquids, high boiling organic liquids, pest control agents such as pesticides, fungicides, insecticides, etc., an emulsifying agent, a suspending agent, a penetrating agent, a wetting agent, a thickening agent, a stabilizer, nutrients, microbial agents, fertilizers, herbicides, etc. The slurry may be formed by combining the components in any order, followed by mixing.

In one embodiment, the particle mixture is applied as a slurry that contains the low boiling point organic liquids can contain about 30% by weight or more and about 99.9% by weight or less of water, about 0.1% by weight or more and about 60% by weight or less of the particle mixture. In another embodiment, the slurry contains about 50% by weight or more and about 99.75% by weight or less of water (which may include the low boiling organic liquids), about 0.25% by weight or more and about 50% by weight or less of the particle mixture. In yet another embodiment, the slurry contains about 60% by weight or more and about 99.5% by weight or less of water (which may include the low boiling organic liquids), about 0.5% by weight or more and about 40% by weight or less of the particle mixture.

The slurry is applied to the target surfaces by spraying, or other suitable means. The particle treatment may be applied as one or more layers before or after drying. The amount of material applied varies depending upon a number of factors, such as the identity of the substrate, the purpose of the application, and the identity of the particle, etc. In any given instance, the amount of material applied can be determined by one of ordinary skill in the art. The amount may be sufficient to form a continuous film or intermittent film over all or a portion of the substrate to which the particle treatment is applied.

The particle treatment may form a continuous layer. By continuous, it is meant that, where applied, the resultant dry film is continuous (or substantially continuous). For example, in an embodiment where the upper third of a fruit is covered with particle mixture in accordance with the present invention, the film covering the upper third of the fruit is continuous or substantially continuous while the bottom two-thirds of the fruit is not covered with the particle mixture or forms a spotted or discontinuous film/deposition.

The slurry contains a relatively small amount of solids (low solids slurry). This is an advantage as one may expect to employ a slurry containing 60% or more solids (high solids slurry). In one embodiment, the slurry contains about 75% by weight or more and about 99.9% by weight or less of liquid (water and/or low/high boiling organic liquids), about 0.1% by weight or more and about 25% by weight or less of the particle or premix. In another embodiment, the slurry contains about 90% by weight or more and about 99.75% by weight or less of liquid and about 0.25% by weight or more and about 10% by weight or less of the particle or premix. In yet another embodiment, the slurry contains about 95% by weight or more and about 99.5% by weight or less of liquid about 0.5% by weight or more and about 5% by weight or less of the particle or premix.

The premix or the slurry may contain an additive such as a pest control agent such as pesticides, fungicides, molluscicides, insecticides, acaracides, bactericides, herbicides, antibiotics, antimicrobials, nemacides, rodenticides, entomopathogens, pheromones, attractants, plant growth regulators, insect growth regulators, chemosterilants, microbial pest control agents, repellents, viruses, phagostimulents, plant nutrients, etc., an emulsifying agent, a suspending agent, a penetrating agent, a wetting agent, a thickening agent, a stabilizer, nutrients, microbial agents, fertilizers, herbicides, and the like. In one embodiment, the premix or slurry contains about 0.01% by weight or more and about 10% by weight or less of one or more additives. In another embodiment, the particle mixture contains about 0.1% by weight or more and about 5% by weight or less of one or more additives.

The volumized film may be applied as one or more layers. After application, the liquid evaporates leaving a volumized film. The amount of material applied varies depending upon a number of factors, such as the identity of the substrate, the purpose of the application, and the identity of the particle, etc. In any given instance, the amount of material applied can be determined by one of ordinary skill in the art. The amount may be sufficient to form a continuous film or intermittent film over all or a portion of the substrate to which the volumized film is applied. The particle film has a thickness suitable to form a volumized system, which is typically thicker (taller) than a film that is dispersed and spread.

When employing certain particles on plants, the volumized particle film allows or blocks, if desired, transmission of PAR while scattering, reflecting, or otherwise blocking undesirable infrared and ultraviolet light.

In one embodiment, the volumized film contains from about 70% to about 99.9% by weight of a particle, from about 0.05% to about 10% by weight of a polymeric film forming material, and from about 0.05% to about 10% by weight of a structuring agent. In another embodiment, the volumized film contains from about 80% to about 99% by weight of a particle, from about 0.5% to about 5% by weight of a polymeric film forming material, and from about 0.5% to about 5% by weight of a structuring agent.

In one embodiment, the volumized film contains from about 70% to about 99.9% by weight of a particle, from about 0.05% to about 10% by weight of a water-insoluble cross-linkable polymeric film forming material, and from about 0.05% to about 10% by weight of a cross-linking agent. In another the volumized film contains from about 80% to about 99% by weight of a particle, from about 0.5% to about 5% by weight of a water-insoluble cross-linkable polymeric film forming material, and from about 0.5% to about 5% by weight of a cross-linking agent.

Low solids content means that the volumized film contains about 60% or less particles by volume. In another embodiment, the volumized film contains about 40% or less particles by volume. In yet another embodiment, the volumized film contains about 25% or less particles by volume.

Figure 2:
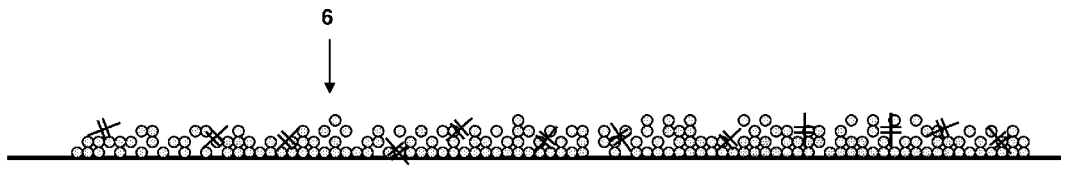

FIGS. 1 and 2 show film-forming spreading of a volumized film of particle 2 on a hydrophilic surface. Use of a volumizing agent 4 forms a film that dries to a thick, opaque and uniform film 6 on hydrophilic surfaces.

Figure 3:
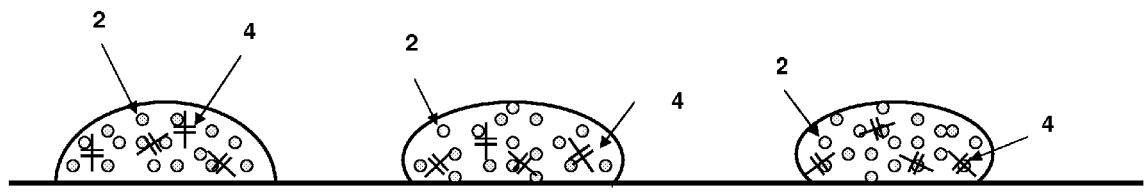
Figure 4:
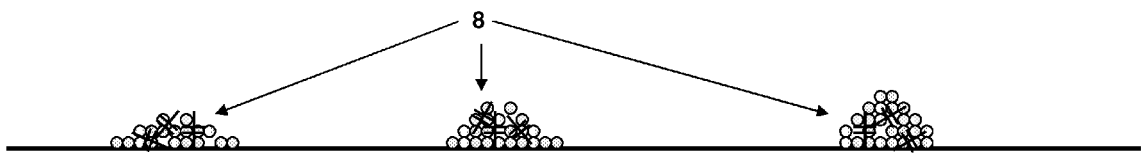

FIGS. 3 and 4 show non-spreading volumized film on a hydrophobic surface using a volumizing agent 4. Delivering particles 2 in slurry creates heavy (usually bright white) spotty volumized deposits 8 on hydrophobic surfaces creating a desirable effect, for example, as a repellent for certain insects.

Figure 5:
Figure 6:

FIGS. 5 and 6 show a non-depositing film on a hydrophobic surface. Delivered particles 2 with volumizing agents 4 make a slurry that is highly incompatible with the hydrophobic surface and either does not deposit or deposits with little volume 10; but still can deposit on the hydrophilic portion of the target. See contrasting high deposition in FIGS. 1 and 2. In grapes and tomato, the fruit are hydrophobic but the leaves are hydrophilic. It can be desirable to coat the leaves but deposit little on the berries.

Figure 7:
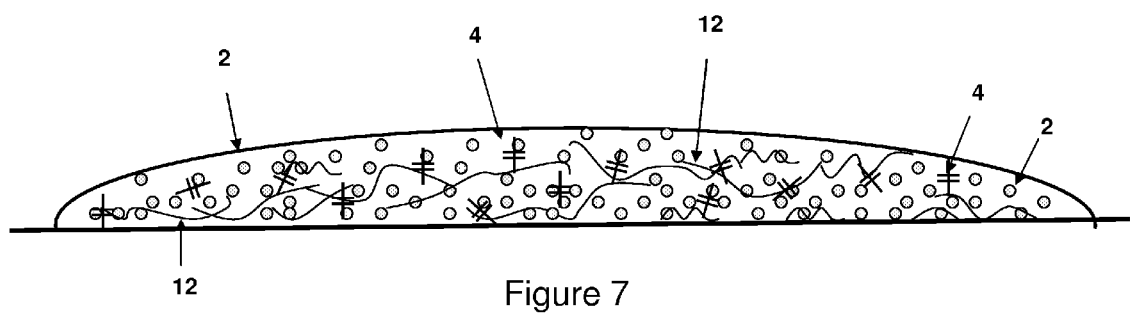
Figure 8:
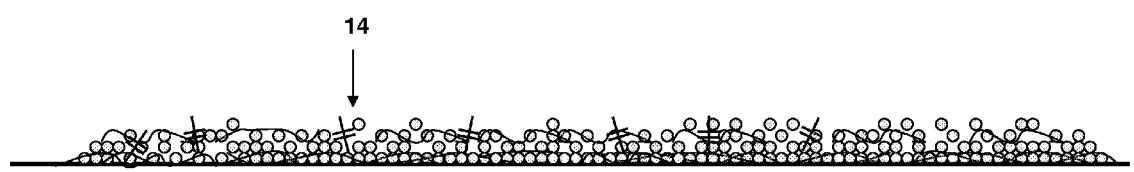

FIGS. 7 and 8 show film-forming spreading and volumizing of particles 2 on both hydrophobic and hydrophilic surfaces with a volumizing agent 4 plus a spreader 12. Use of a conventional spreader 12 with a volumizing agent that does not spread by itself on hydrophobic surfaces 4 creates an improved film deposition 14. The surfactant promotes spreading while the volumizing agent increases deposition on the target surface.

The following examples illustrate the present invention. Unless otherwise indicated in the following examples and elsewhere in the specification and claims, all parts and percentages are by weight, all temperatures are in degrees Centigrade, and pressure is at or near atmospheric pressure.

In the following Comparatives and Inventive Examples, the hydrous kaolin and calcined kaolin used were from Engelhard Corporation (now BASF Catalysts LLC). The compositions were applied to two different media and photographed. The photographs appear as FIGS. 9-25 where the Red Delicious apple is on the left and tomato leaves are on the right. The Red Delicious apple surface is hydrophobic while tomato leaves are hydrophilic.

Comparative A

Commercial Surround WP crop protectant was applied to a Red Delicious apple and tomato leaves. We did not add a volumizing agent or conventional spreader.

Figure 9:
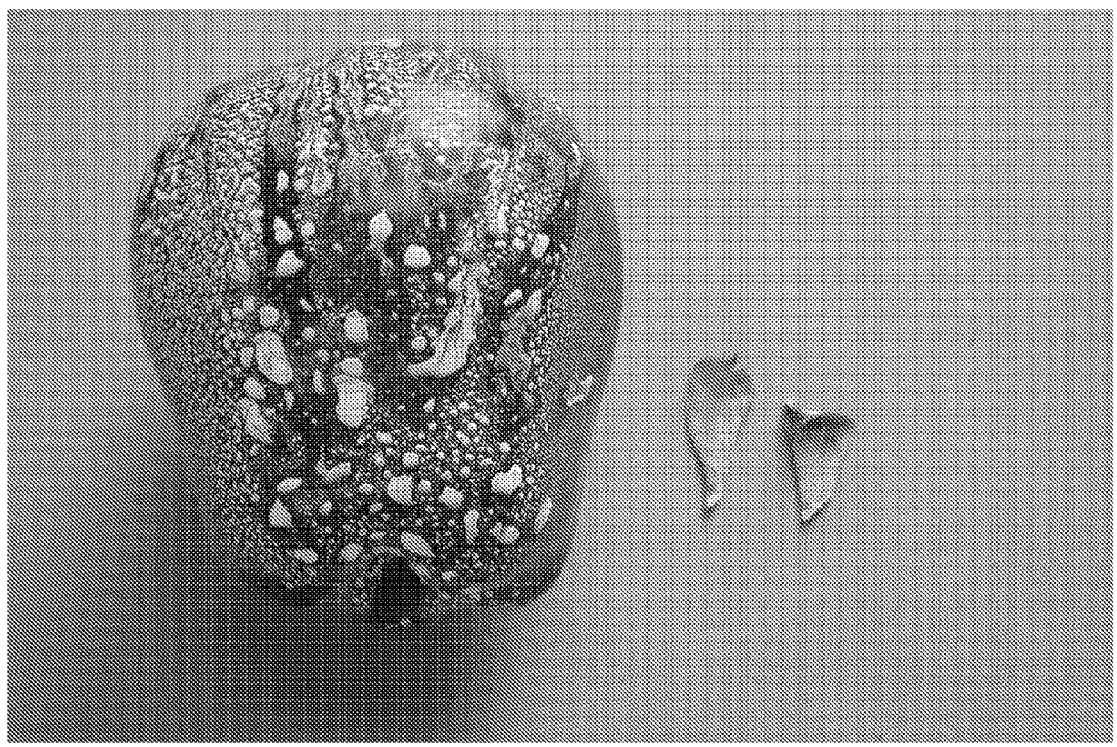

As shown in FIG. 9, Surround WP is spotty on the apple but forms adequate films on the tomato leaves.

Comparative B

Commercial hydrous kaolin was applied to a Red Delicious apple and tomato leaves. We did not add a volumizing agent or conventional spreader.

Figure 10:
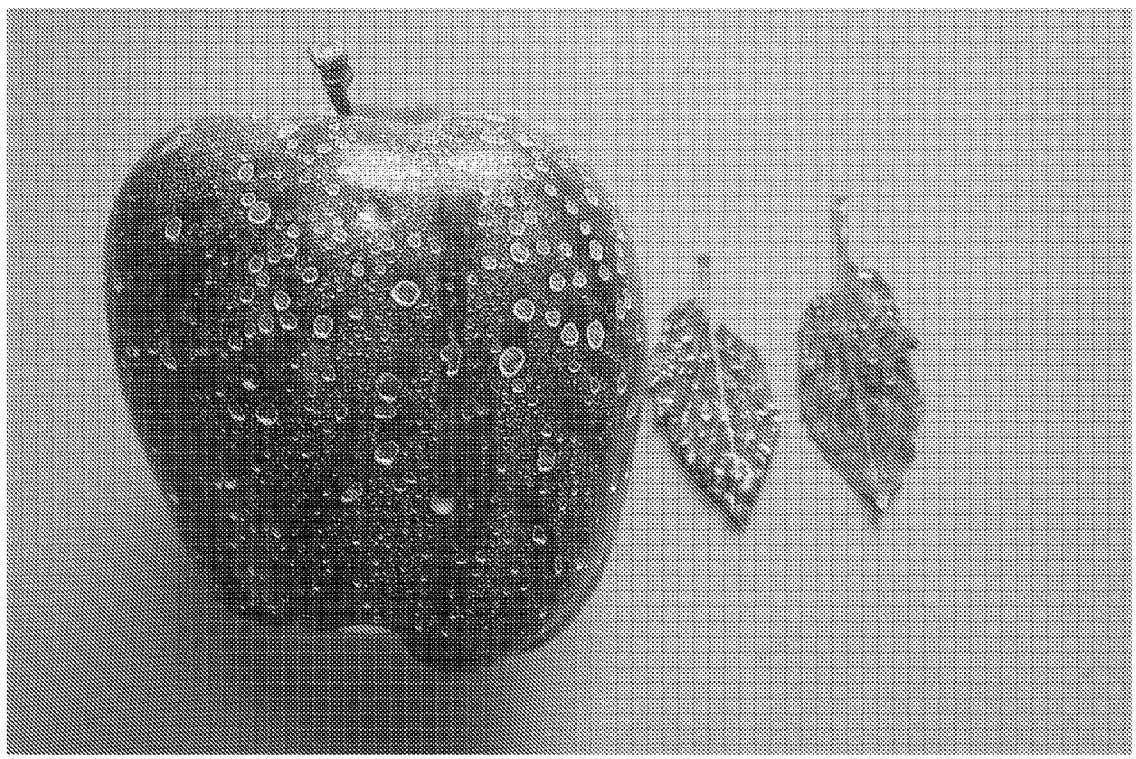

As shown in FIG. 10, film formation is poor on both media.

Comparative C

Figure 24:
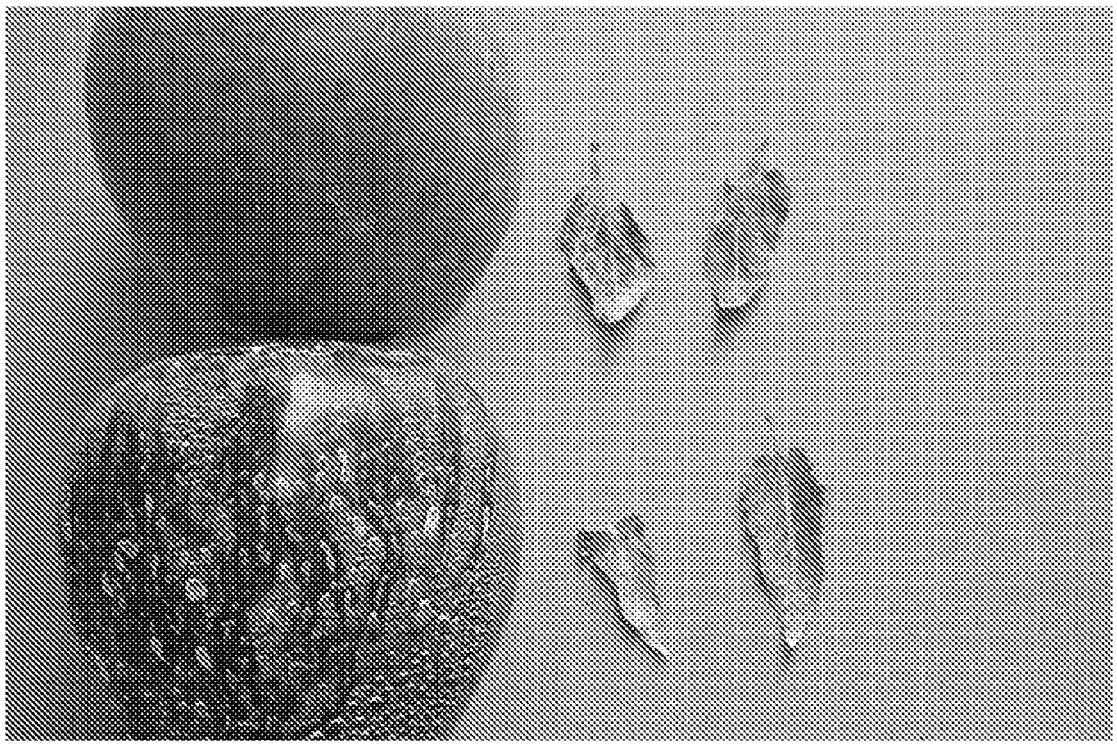

Commercial calcined kaolin was applied to a Red Delicious apple and tomato leaves with only a spreader. As shown in FIG. 24, film formation is very thin on both media.

Comparative D

Figure 25:

Commercial hydrous kaolin was applied to a Red Delicious apple and tomato leaves with only a spreader. As shown in FIG. 25, film formation is extremely thin on both media and the film can barely be seen.

Inventive Example 1

A composition was formed by combining hydrous kaolin with a volumizing agent that does not spread on hydrophobic surfaces. The volumizing agent used was a cationic polymer of polydiallyldimethylammonium chloride in an amount of 2.5% of a 20% solution. The composition was applied to a Red Delicious apple and tomato leaf.

Figure 11:
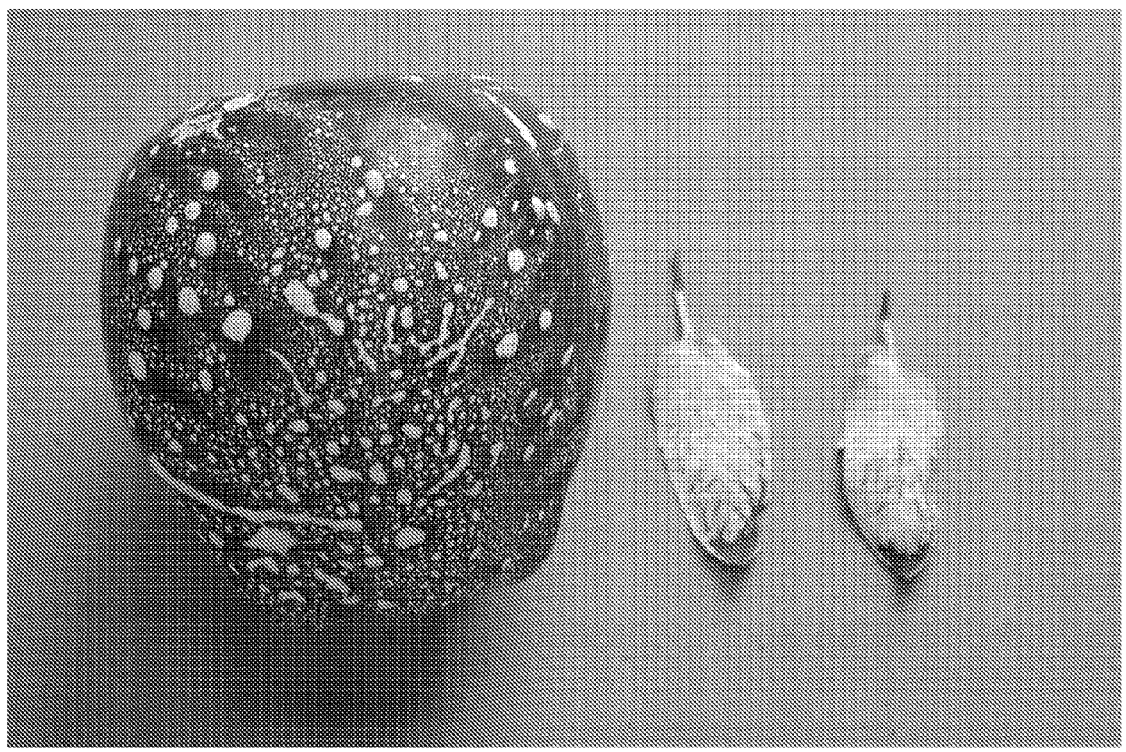

A photograph of the resulting apple and tomato leaves is shown as FIG. 11. Deposition is extremely spotty on the apple and uniform and heavy on the tomato leaves.

Inventive Example 2

A composition was formed by combining hydrous kaolin with a volumizing agent that does not spread on hydrophobic surfaces. The volumizing agent used was hydroxylethyl cellulose in an amount of 0.35%. The composition was applied to a Red Delicious apple and tomato leaf.

Figure 12:
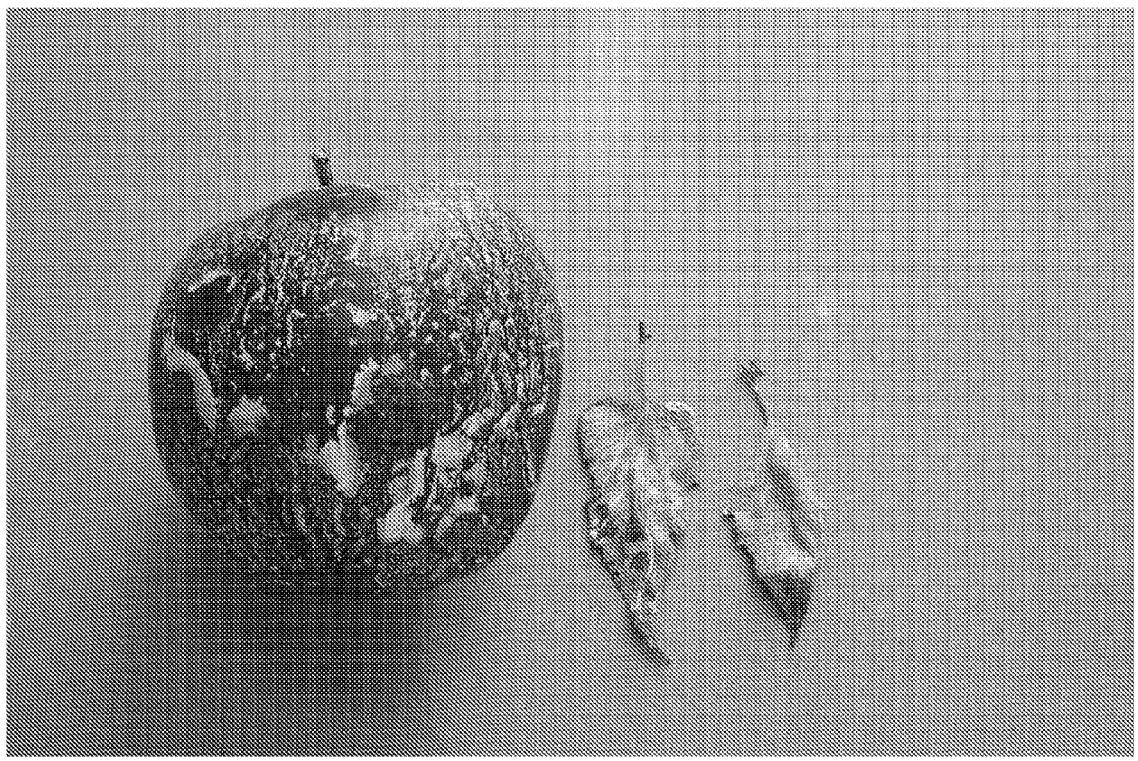

A photograph of the resulting apple and tomato leaf is shown as FIG. 12. Deposition is uneven, irregular, and blotchy on the apple and uniform and heavy on the tomato leaves.

Inventive Example 3

A composition was formed by combining hydrous kaolin with a volumizing agent that does not spread on hydrophobic surfaces. The volumizing agent used was carboxy methyl cellulose and in an amount of 0.35%. The composition was applied to a Red Delicious apple and tomato leaves.

Figure 13:
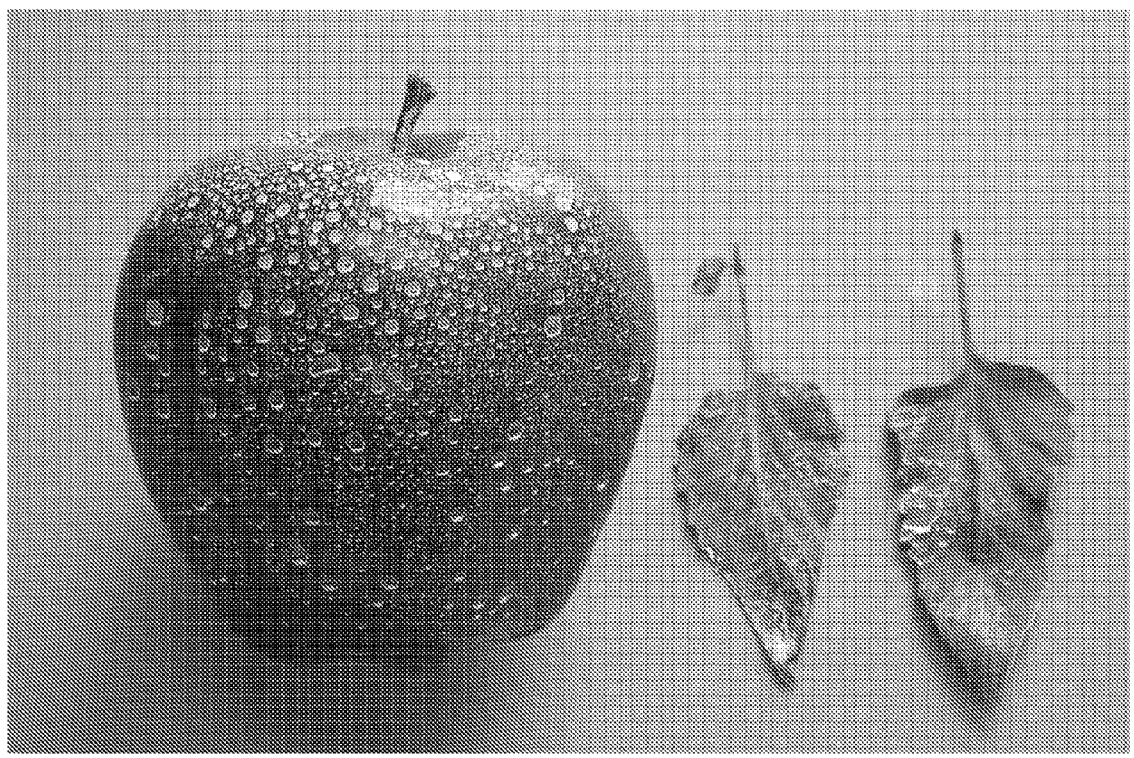

A photograph of the resulting apple and tomato leaf is shown as FIG. 13. Deposition is spotty on the apple and adequate on the tomato leaves.

Inventive Example 4

Inventive Example 1 was repeated except that a commercial silicone spreader was added. The amount of spreader used was 0.25% in the top row while the amount of spreader used was 0.025% in the bottom row.

Figure 14:
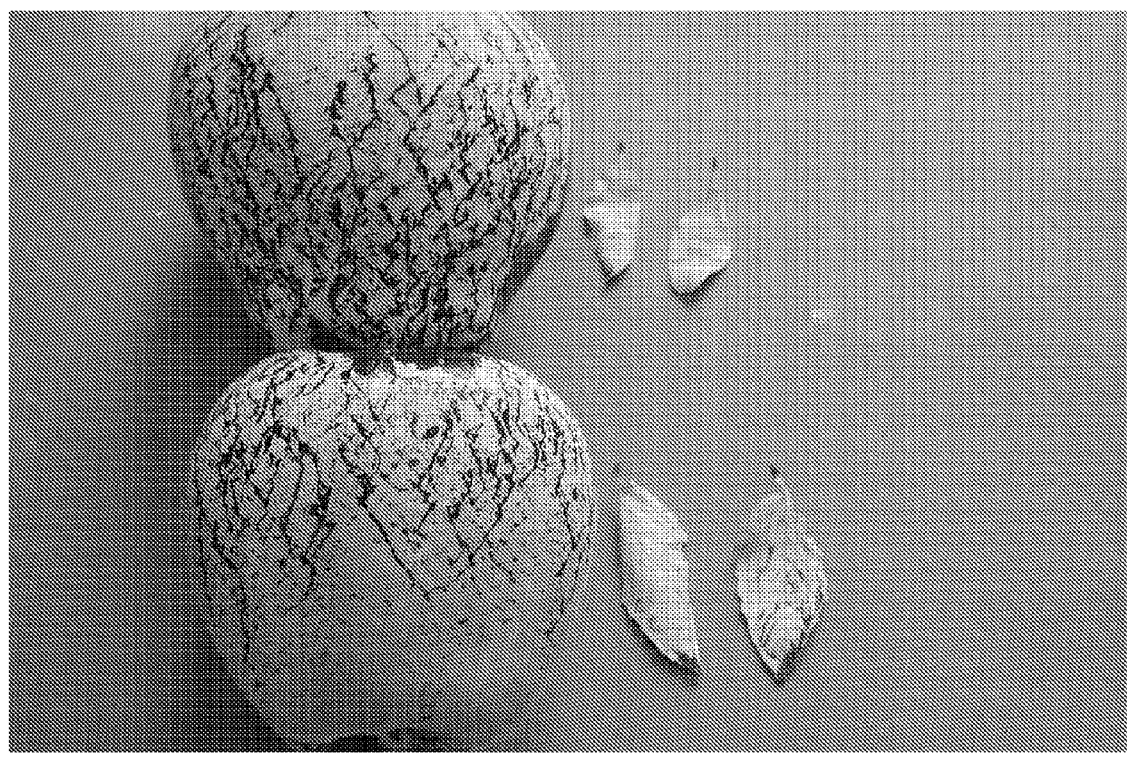

A photograph of the resulting apple and tomato leaf is shown in FIG. 14. Film-forming spreading was achieved as deposition is heavy and even on both media.

Comparative E

Commercial calcined kaolin was applied to a Red Delicious apple and tomato leaves. We did not add a volumizing agent or conventional spreader.

Figure 15:
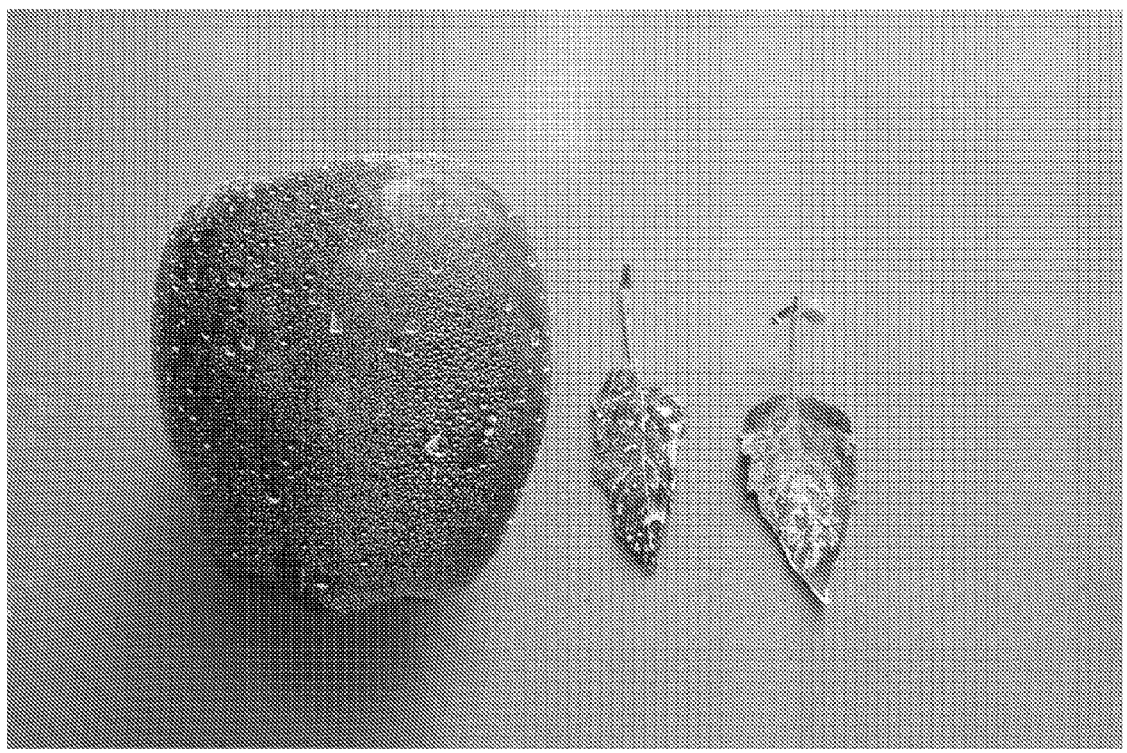

As shown in FIG. 15, film formation is spotty on the apple and adequate on the tomato leaves.

Inventive Example 5

Inventive Example 1 was repeated except that calcined kaolin was used.

Figure 16:
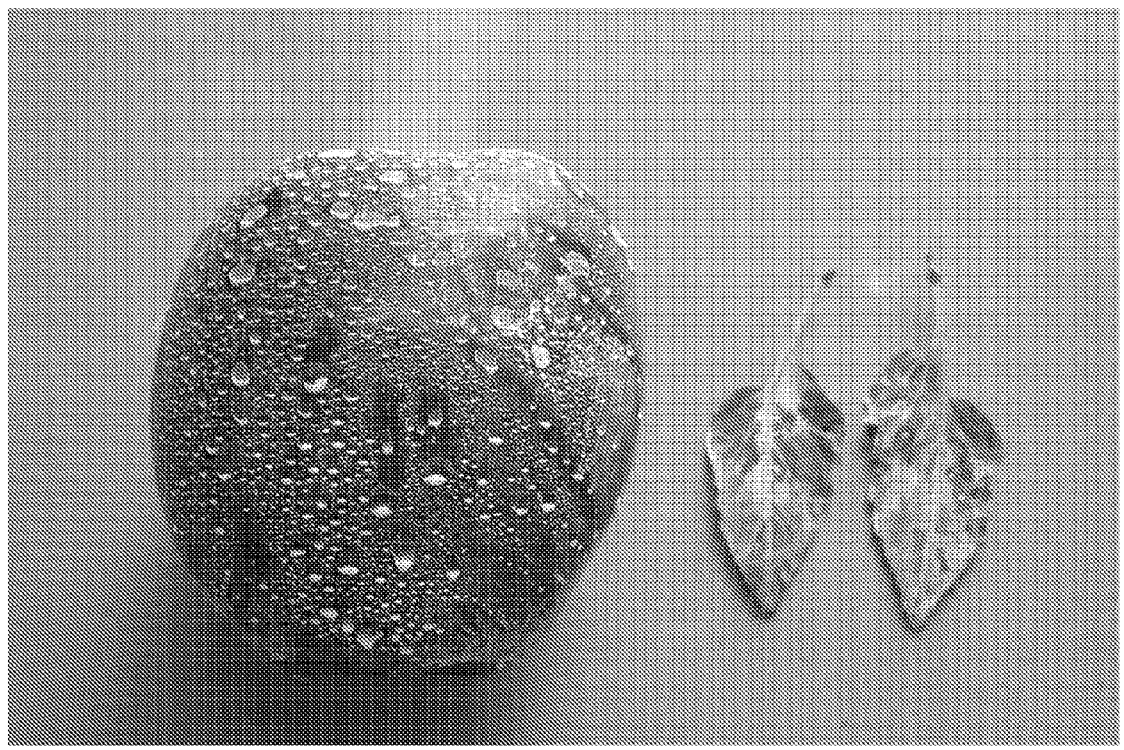

A photograph of the resulting apple and tomato leaf is shown in FIG. 16. Comparable to Inventive Example 1, film formation is spotty on the apples and uniform and heavy on the tomato leaves.

Inventive Example 6

Inventive Example 2 was repeated except that calcined kaolin was used.

Figure 17:
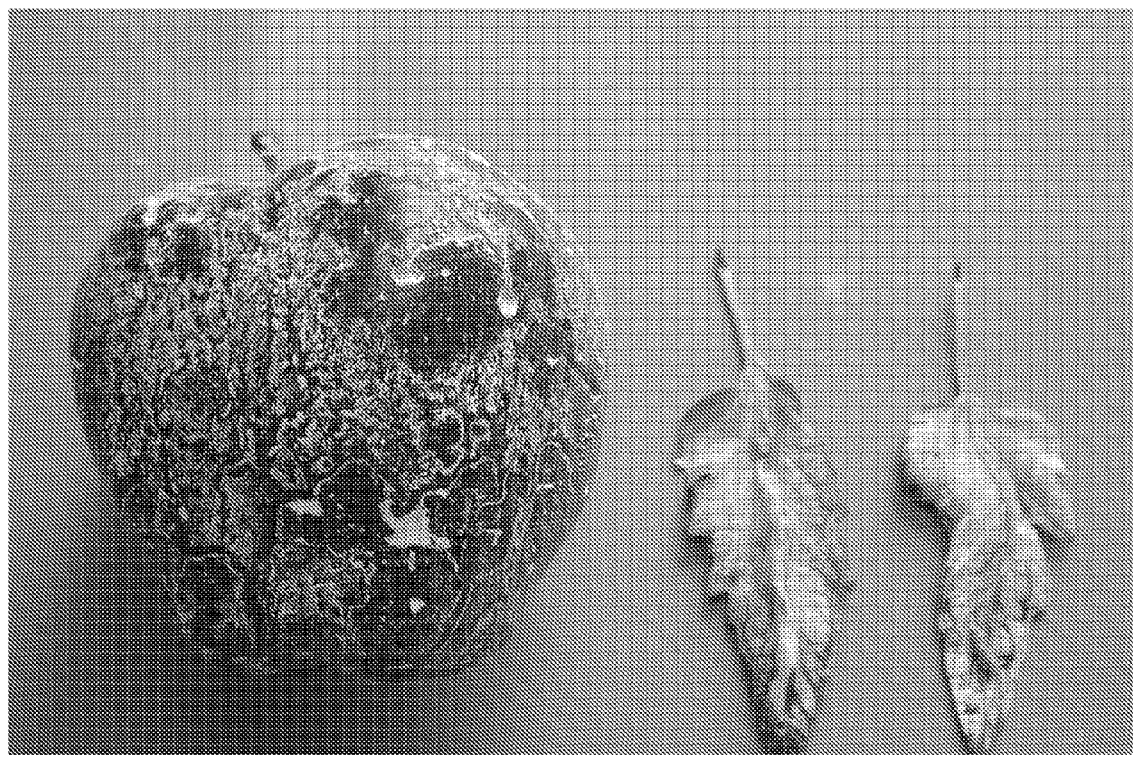

A photograph of the resulting apple and tomato leaf is shown in FIG. 17. Comparable to Inventive Example 2, film formation is spotty on the apples and excellent on the tomato leaves.

Inventive Example 7

Inventive Example 3 was repeated except that calcined kaolin was used.

Figure 18:
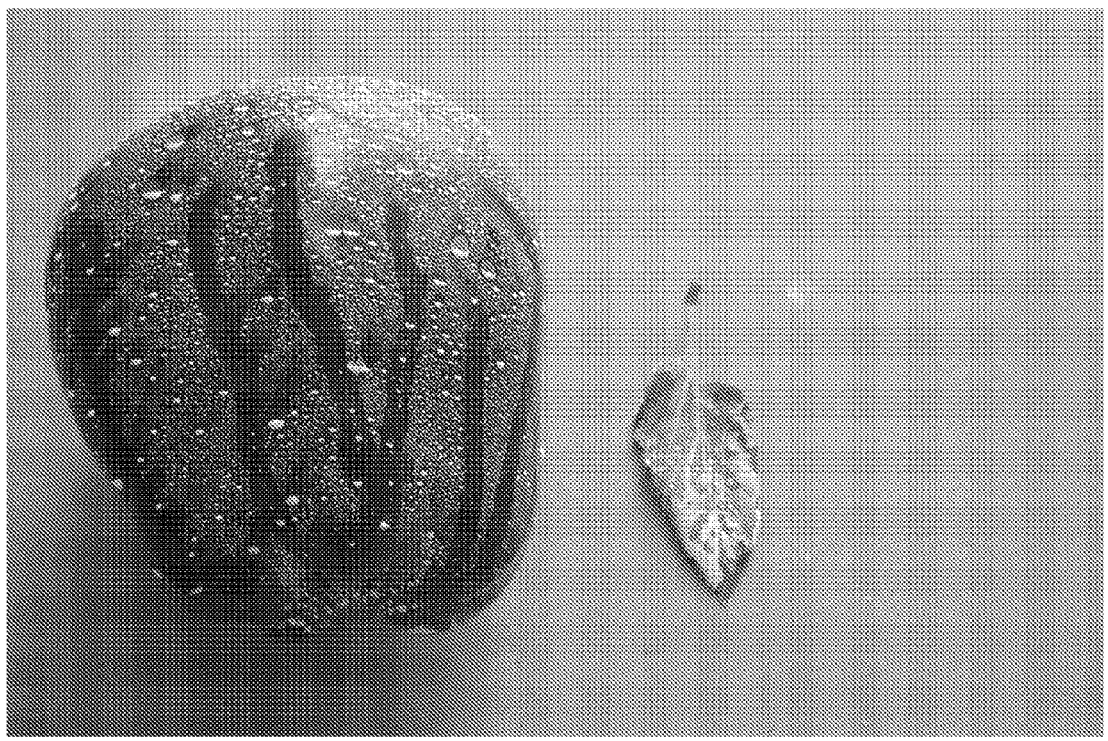

A photograph of the resulting apple and tomato leaf is shown in FIG. 18. Comparable to Inventive Example 3, film formation is spotty and runny on the apples but uniform and heavy on the tomato leaf.

Inventive Example 8

Inventive Example 4 was repeated except that calcined kaolin was used.

Figure 19:
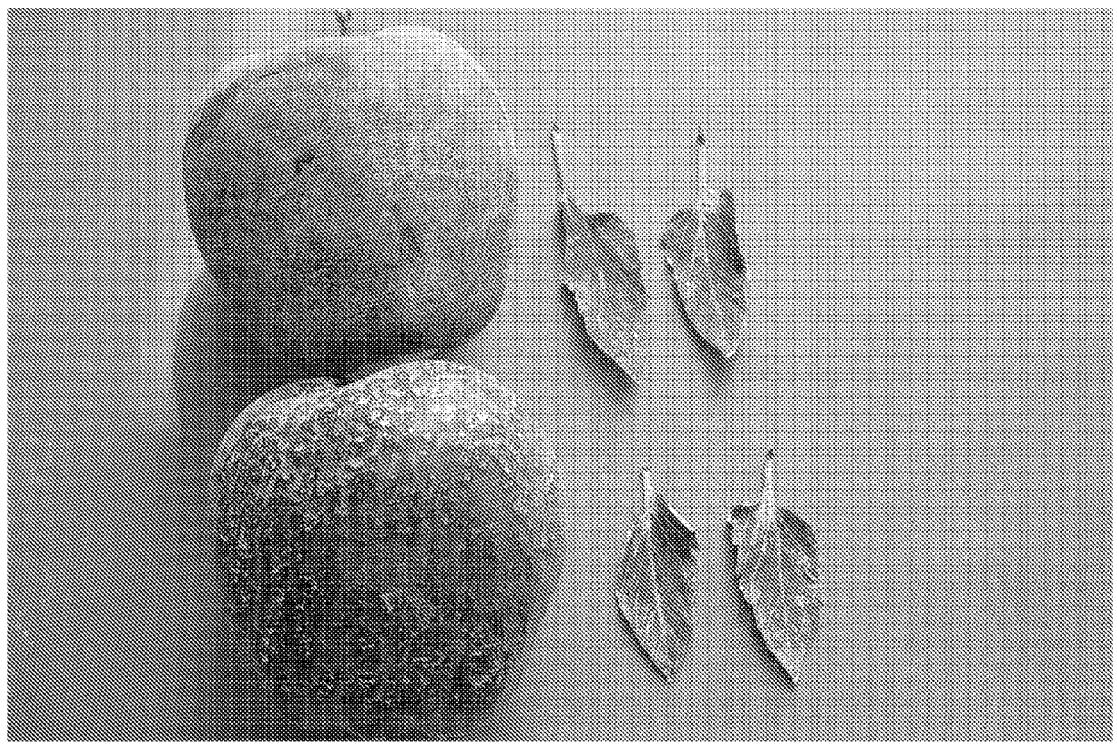

As shown in FIG. 19, uniform and heavy film formations were developed on both media.

Inventive Example 9

Inventive Example 8 was repeated except that the particles were a blend of 50% calcined kaolin and 50% hydrous kaolin.

Figure 20:
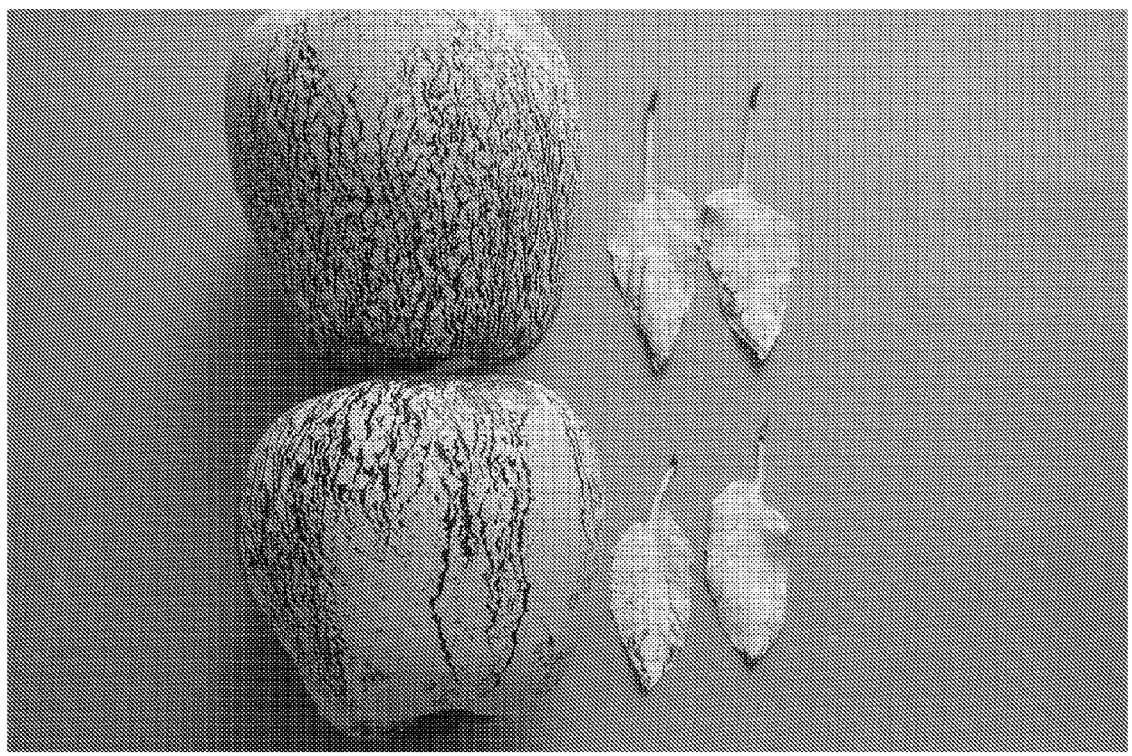

As shown in FIG. 20, film formation on both media was superior with heavy and even depositions.

Inventive Example 10

Inventive Example 6 was repeated expect that the particles were a blend of 50% calcined kaolin and 50% hydrous kaolin.

Figure 21:
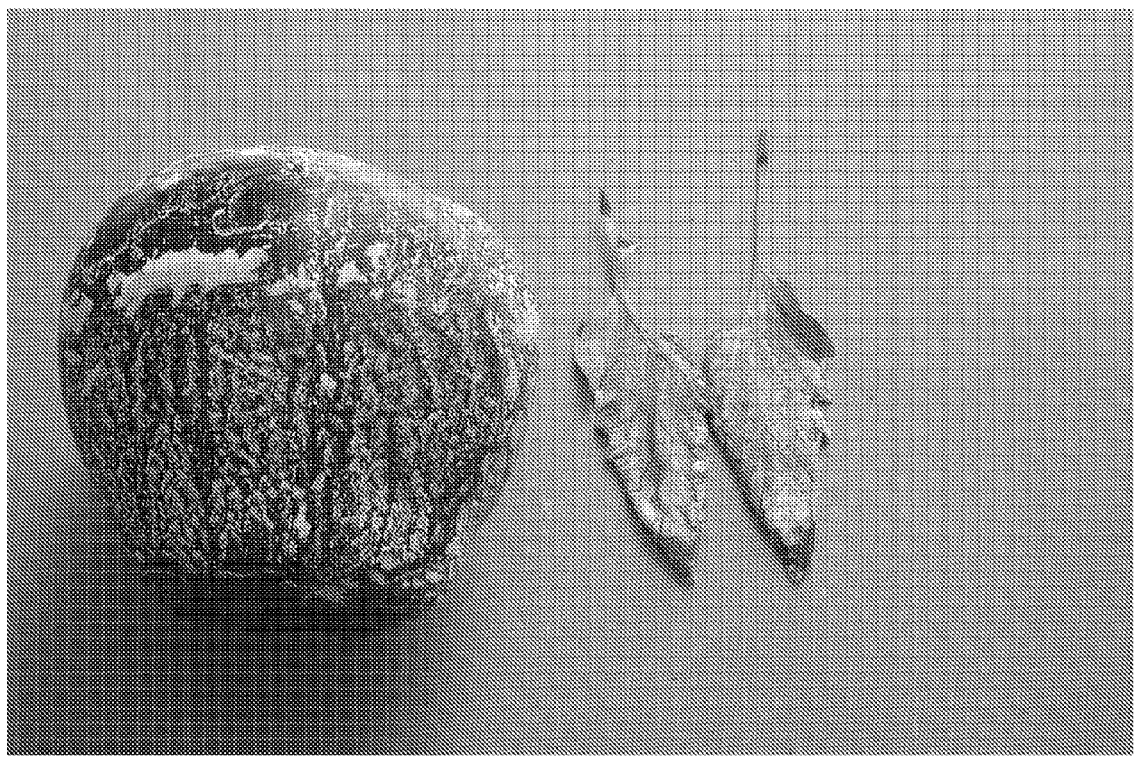

As shown in FIG. 21, the film on the tomato is equal to FIG. 17 which is 100% calcined kaolin.

Inventive Example 11

Inventive Example 7 was repeated expect that the particles were a blend of 50% calcined kaolin and 50% hydrous kaolin.

Figure 22:
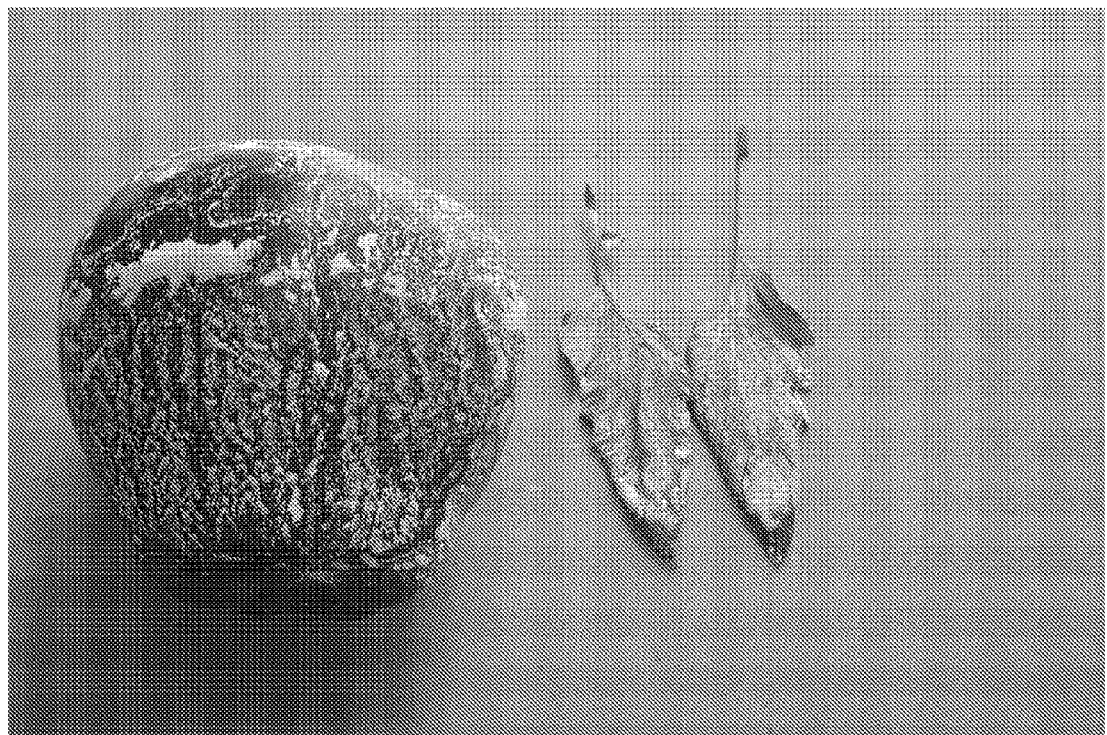

As shown in FIG. 22, the film on the tomato is equal to FIG. 18 which is 100% calcined kaolin.

Inventive Example 12

Inventive Example 5 was repeated expect that the particles were a blend of 50% calcined kaolin and 50% hydrous kaolin.

Figure 23:
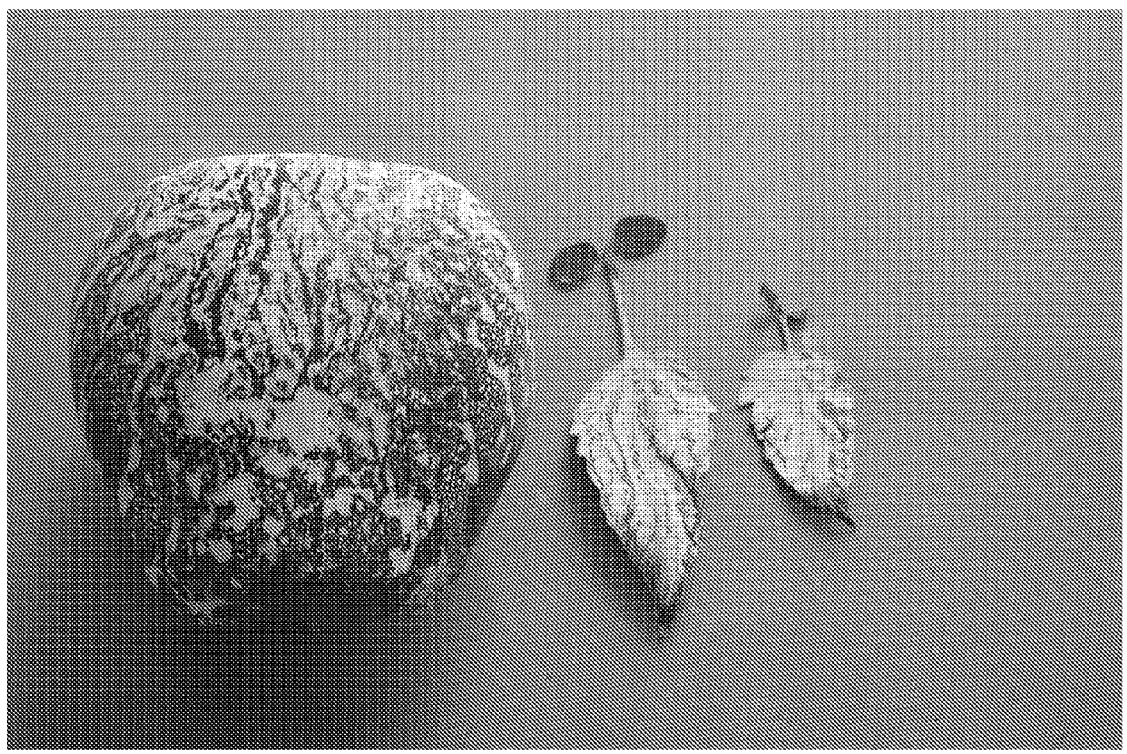

As shown in FIG. 23, the film on the tomato is superior to FIG. 16 which is 100% calcined kaolin.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of treating plants comprising:
   applying a slurry containing water and a composition that is capable of forming a particle film to horticultural crops to form a film having a thickness of about 3 μm to about 3,000 μm, said composition comprising:
   (a) about 70% to about 99.9% by weight of kaolin particles having a median individual particle size of about 3 μm or less;
   (b) at least one volumizing agent selected from the group consisting of:
   (i) cellulose selected from the group consisting of ethyl hydroxy ethyl cellulose, hydroxy ethyl cellulose, hydroxy propyl cellulose, hydroxy ethyl methyl cellulose, hydroxy propyl methyl cellulose, methyl cellulose, ethyl cellulose, and ethyl methyl cellulose, present in an amount of 0.35% to 5% by weight; and
   (ii) non-cellulosic component which is polydiallyldimethylammonium chloride present in an amount of 0.35% to 5% by weight.

2. The method of claim 1, wherein said kaolin particles are selected from the group consisting of water processed kaolin, air pressed kaolin, and hydrous kaolin.

3. The method of claim 2 wherein the volumizing agent is a cellulose selected from the group consisting of ethyl hydroxy ethyl cellulose, hydroxy ethyl cellulose, hydroxy propyl cellulose, hydroxy ethyl methyl cellulose, hydroxy propyl methyl cellulose, methyl cellulose, ethyl cellulose, and ethyl methyl cellulose.

4. The method of claim 2 wherein the volumizing agent is hydroxy ethyl cellulose.

5. The method of claim 2 wherein the volumizing agent is polydiallydimethylammonium chloride.

6. The method of claim 1 additionally comprising a spreader (c).

7. The method of claim 1 wherein said particles (a) comprise a blend of at least two different particles.

8. The method of claim 7 wherein said blend is calcined kaolin and hydrous kaolin.

9. The method of claim 1 wherein composition comprises at least 0.5% by weight of volumizing agents.

10. The method of claim 1 wherein composition comprises from about 0.5% to 5% by weight of volumizing agents.

11. A method of treating plants comprising: applying a slurry containing water and a composition to horticultural crops to form a film having a thickness of about 3 μm to about 3,000 μm said composition comprising:
    (a) about 70% to about 99.9% by weight of kaolin particles having a median individual particle size of about 3 μm or less;
    (b) at least one volumizing agent selected from the group consisting of (i) 0.35% to 5% by weight hydroxy ethyl cellulose; and (ii) 0.35% to 5% by weight polydiallyldimethylammonium chloride, and (c) at least one spreader.

12. The method of claim 11 further comprising an effective amount of a crosslinking agent.

13. The method of claim 11 wherein the volumizing agent is hydroxy ethyl cellulose.

14. The method of claim 11 wherein the volumizing agent is polydiallydimethylammonium chloride.

15. The method of claim 13 wherein the particles are hydrous kaolin.

* * * * *